US005747514A

United States Patent [19]
Beckett et al.

[11] Patent Number: 5,747,514
[45] Date of Patent: May 5, 1998

[54] METALLOPROTEINASE INHIBITORS

[75] Inventors: Raymond Paul Beckett; Mark Whittaker; Andrew Miller; Fionna Mitchell Martin, all of Cowley, United Kingdom

[73] Assignee: British Biotech Pharmaceuticals Limited, Oxford, England

[21] Appl. No.: 685,330

[22] Filed: Jul. 19, 1996

Related U.S. Application Data

[63] Continuation-in-part of PCT/GB95/00111, Jan. 20, 1995 published as WO95/19956, Jul. 27, 1995.

[30] Foreign Application Priority Data

Jan. 20, 1994 [GB] United Kingdom ............ 9401034
Aug. 2, 1994 [GB] United Kingdom ............ 9415619

[51] Int. Cl.$^6$ .................... C07D 213/75; A61K 31/44
[52] U.S. Cl. ............... 514/352; 514/362; 514/363; 514/370; 514/372; 514/477; 514/626; 546/309; 548/135; 548/139; 548/192; 548/206; 549/69; 564/153; 564/155
[58] Field of Search ............. 546/309; 514/352, 514/362, 363, 370, 372, 487, 626; 548/192, 206, 135, 139; 549/69; 564/153, 155

[56] References Cited

U.S. PATENT DOCUMENTS 4,599,361   7/1986   Dickens et al. ............ 514/575

FOREIGN PATENT DOCUMENTS

| | | |
|---|---|---|
| 236 872 | 9/1987 | European Pat. Off. . |
| 274 453 | 7/1988 | European Pat. Off. . |
| 489 577 | 6/1992 | European Pat. Off. . |
| 489 579 | 6/1992 | European Pat. Off. . |
| 497 192 | 8/1992 | European Pat. Off. . |
| 574 758 | 12/1993 | European Pat. Off. . |
| WO 90/05716 | 5/1990 | WIPO . |
| WO 90/05719 | 5/1990 | WIPO . |
| WO 91/02716 | 3/1991 | WIPO . |
| WO 92/13831 | 8/1992 | WIPO . |
| WO 92/17460 | 10/1992 | WIPO . |
| WO 92/21360 | 12/1992 | WIPO . |
| WO 92/22523 | 12/1992 | WIPO . |
| WO 93/09090 | 5/1993 | WIPO . |
| WO 93/09097 | 5/1993 | WIPO . |
| WO 93/14112 | 7/1993 | WIPO . |
| WO 93/24449 | 9/1993 | WIPO . |
| 9320047 | 10/1993 | WIPO . |
| WO 93/20047 | 10/1993 | WIPO . |
| WO 93/24475 | 12/1993 | WIPO . |
| 9424140 | 10/1994 | WIPO . |
| WO 94/24140 | 11/1994 | WIPO . |

OTHER PUBLICATIONS

J. Chem. Society, Perkin Transation, vol. 1, No. 9, 1975, pp. 857–860, Broughton et al.
Broughton, "Studies Concerning the Antibiotic Actinonin. Part VIII. Structure–Activity Relationships in the Actinonin Series," *J. Chem. Soc.*, 9:857–860 (1975).
Cawston, et al., "Mammalian Collagenases, " *Meth. In Enzymol.*, 80:711–722 (1981).
Cawston, et al., "A Rapid and Reproducible Assay for Collagenase Using [1–$^{14}$C]Acetylated Collagen, " *Ana. Biochem.*, 99:340–345 (1979).
Cawston, et al., "Purification of Rabbit Bone Inhibitor of Collagenase," *Biochem. J.*, 195:159–165 (1981).
Devlin, et al., "Studies Concerning the Antibiotic Actinonin. Part III. Synthesis of Structural Analogues of Actinonin by the Anhydride–Imide Method," *J.C.S. Perkin Trans 1*, 830–841 (1975).
Sellers, "Separation in Latent Forms of Distinct Enzymes that When Activated Degrade Collagen, Gelatin and Proteoglycans," *Biochem. J.* 171:493–496 (1978).
Woessner, "Matrix Metalloproteinases and their Inhibitors in Connective Tissue Remodeling," *FASEB J.*, 5:2145–2154, (1991).

*Primary Examiner*—Zinna Northington Davis
*Attorney, Agent, or Firm*—Banner & Witcoff, Ltd.

[57] ABSTRACT

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumor necrosis factor from cells.

27 Claims, No Drawings

METALLOPROTEINASE INHIBITORS

This is a continuation-in-part of International Application PCT/GB95/00111, with an international filing date of Jan. 20, 1995.

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumour necrosis factor from cells.

BACKGROUND TO THE INVENTION

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas. However, the relative contributions of individual MMPs in any of the above disease states is not yet fully understood.

Metalloproteinases are characterised by the presence in the structure of a zinc(II) ionic site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (J. F. Woessner, FASEB J, 1991, 5, 2145-2154). Many known MMP inhibitors are peptide derivatives, based on naturally occuring amino acids, and are analogues of the cleavage site in the collagen molecule. A recent paper by Chapman et al. (J. Med. Chem. 1993, 36, 4293-4301) reports some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the zinc (II) site in the MMP, and known classes include those in which the zinc binding group is a hydroxamic acid, carboxylic acid, sulphydryl, and oxygenated phosphorus (e.g. phosphinic acid and phosphonamidate including aminophosphonic acid) groups.

Two known classes of pseudopeptide or peptide mimetic MMP inhibitors have a hydroxamic acid group and a carboxylic group respectively as their zinc binding groups. With a few exceptions, such known MMPs may be represented by the structural formula (I)

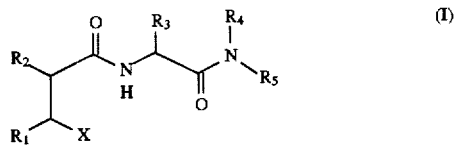

in which X is the zinc binding hydroxamic acid (—CONHOH) or carboxylic acid (—COOH) group and the groups $R_1$ to $R_5$ are variable in accordance with the specific prior art disclosures of such compounds. Examples of patent publications disclosing such structures are given below.

In such compounds, it is generally understood in the art that variation of the zinc binding group and the substituents $R_1$, $R_2$ and $R_3$ can have an appreciable effect on the relative inhibition of the metalloproteinase enzymes. The group X is thought to interact with metalloproteinase enzymes by binding to a zinc(II) ion in the active site. Generally the hydroxamic acid group is preferred over the carboxylic acid group in terms of inhibitory activity against the various metalloproteinase enzymes. However, the carboxylic acid group in combination with other substituents can provide selective inhibition of gelatinase (EP-489,577-A). The $R_1$, $R_2$ and $R_3$ groups are believed to occupy respectively the P1, P1' and P2' amino acid side chain binding sites for the natural enzyme substrate. There is evidence that a larger $R_1$ substituent can enhance activity against stromelysin, and that a ($C_1$–$C_6$)alkyl group (such as iso-butyl) at $R_2$ may be preferred for activity against collagenase whilst a phenylalkyl group (such as phenylpropyl) at $R_2$ may provide selectivity for gelatinase over the other metalloproteinases.

Tumour necrosis factor (herein referred to as "TNF") is a cytokine which is produced initially as a cell-associated 28 kD precursor. It is released as an active, 17 kD form, which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury. Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

Recently, WO 93/20047 disclosed a class of hydroxamic acid based MMP inhibitors which also are active in inhibiting TNF production.

As mentioned above, MMP inhibitors have been proposed with hydroxamic acid or carboxylic acid zinc binding groups. The following patent publications disclose hydroxamic acid-based MMP inhibitors:

| | |
|---|---|
| US 4599361 | (Searle) |
| EP-A-0236872 | (Roche) |
| EP-A-0274453 | (Bellon) |
| WO 90/05716 | (British Bio-technology) |
| WO 90/05719 | (British Bio-technology) |
| WO 91/02716 | (British Bio-technology) |
| EP-A-0489577 | (Celltech) |
| EP-A-0489579 | (Celltech) |
| EP-A-0497192 | (Roche) |
| WO 92/13831 | (British Bio-technology) |
| WO 92/17460 | (SmithKline Beecham) |
| WO 92/22523 | (Research Corporation Technologies) |
| WO 93/09090 | (Yamanouchi) |
| WO 93/09097 | (Sankyo) |
| WO 93/20047 | (British Bio-technology) |
| WO 93/24449 | (Celltech) |
| WO 93/24475 | (Celltech) |
| EP-A-0574758 | (Roche) |

The following patent publications disclose carboxylic acid-based MMP inhibitors:

| | |
|---|---|
| EP-A-0489577 | (Celltech) |
| EP-A-0489579 | (Celltech) |
| WO 93/24449 | (Celltech) |
| WO 93/24475 | (Celltech) |

BRIEF DESCRIPTION OF THE INVENTION

This invention is based on the finding that in compounds of formula (I) above wherein X is a hydroxamic acid or carboxylic acid group, an aromatic or heteroaryl $R_4$ substituent has in general the unexpected and desirable effect of increasing activity against stromelysin relative to compounds of otherwise similar structure but with the usual $R_4$ substituents, while maintaining activity against collagenase and gelatinase. This finding leads to compounds that are broad spectrum inhibitors of the known metalloproteinases. The class of compounds of the invention also includes compounds in which the ability to inhibit TNF production is improved relative to compounds of otherwise similar structure but with the usual $R_4$ substituents. The class also includes compounds which are orally bioavailable.

In general, metalloproteinase inhibitors known in the art to possess good activity against stromelysin are compounds such as BB-94 (WO 90/05719 Example 2) that possess relatively large substituents at $R_1$. However, BB-94 and compounds with large substituents at $R_1$ tend to be less bioavailable when dosed orally than compounds with smaller or no $R_1$ substituent. A particular advantage of the compounds of the present invention is that the combination of an aromatic or heteroaryl $R_4$ substituent with no $R_1$ substituent or a small $R_1$ substituent can provide oral activity together with broad spectrum activity against the metalloproteinase enzymes, including good potency against stromelysin.

The art does not appear to have recognised the role of an aromatic or heteroaryl $R_4$ substituent in increasing the activity of hydroxamic acid and carboxylic acid based pseudopeptide or peptide mimetic MMP inhibitors against stromelysin. Of the publications relating to hydroxamic acid based MMP inhibitors listed above, only WO 93/09097 (Sankyo) refers to the possibility of a phenyl group in the relevant position. In a structurally different series of MMP inhibitors with phosphinic acid zinc binding groups, WO 93/14112 (Merck) discloses compounds with certain aryl groups in the equivalent position. In neither case is there any comment on the role of that group in the overall structure/ activity relationships of the disclosed compounds. In the field of natural peptide analogues the publication by Chapman et. al. referred to above discloses that aryl groups in the corresponding position to the $R_4$ position of compounds of this invention appear to be preferred for stromelysin activity. WO 92/21360 (Merck) also discloses natural peptide analogues having certain aryl groups in the corresponding position to the $R_4$ position of compounds of this invention. However it is not clear that structure/activity relationships which are true in the field of natural peptide MMP inhibitors will hold true in the field of pseudopeptide or peptide mimetic MMP inhibitors with which this invention is concerned.

DETAILED DESCRIPTION OF THE INVENTION

The present invention provides compounds of general formula I

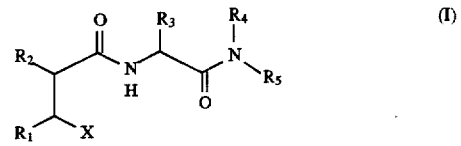

wherein

X is a —$CO_2H$ or —CONHOH group;

$R_1$ is hydrogen; ($C_1$–$C_6$)alkyl; ($C_2$–$C_6$)alkenyl; phenyl; substituted phenyl; phenyl ($C_1$–$C_6$)alkyl); substituted phenyl($C_1$–$C_6$)alkyl; heterocyclyl; substituted heterocyclyl; heterocyclyl($C_1$–$C_6$)alkyl; substituted heterocyclyl($C_1$–$C_6$)alkyl; a group $BSO_nA$— wherein n is 0, 1 or 2 and B is hydrogen or a ($C_1$–$C_6$) alkyl, phenyl, substituted phenyl, heterocyclyl, ($C_1$–$C_6$)acyl, phenacyl or substituted phenacyl group, and A represents ($C_1$–$C_6$)alkyl; amino; protected amino; acylamino; OH; SH; ($C_1$–$C_6$)alkoxy; ($C_1$–$C_6$)alkylamino; di-($C_1$–$C_6$)alkylamino; ($C_1$–$C_6$)alkylthio; aryl ($C_1$–$C_6$) alkyl; amino($C_1$–$C_6$)alkyl; hydroxy($C_1$–$C_6$)alkyl, mercapto($C_1$–$C_6$)alkyl or carboxy($C_1$–$C_6$)alkyl wherein the amino-, hydroxy-, mercapto- or carboxyl-group are optionally protected or the carboxyl-group amidated; lower alkyl substituted by carbamoyl, mono (lower alkyl)carbamoyl, di(lower alkyl)carbamoyl, di(lower alkyl)amino, or carboxy-lower alkanoylamino;

$R_2$ is a ($C_1$–$C_6$)alkyl, ($C_2$–$C_6$)alkenyl, ($C_2$–$C_6$)alkynyl, phenyl($C_1$–$C_6$)alkyl, heteroaryl($C_1$–$C_6$)alkyl, cycloalkyl($C_1$–$C_6$)alkyl or cycloalkenyl($C_1$–$C_6$) alkyl group, any one of which may be optionally substituted by one or more substituents selected from ($C_1$–$C_6$) alkyl, —O($C_1$–$C_6$)alkyl, —S($C_1$–$C_6$)alkyl, halo and cyano (—CN);

$R_3$ is the characterising group of a natural or non-natural α amino acid in which any functional groups may be protected;

$R_4$ is a phenyl or 5- or 6-membered heteroaryl ring wherein any ring nitrogen atom may be oxidised as an N-oxide, which may be optionally fused to a benzene ring or to a 5-, 6- or 7-membered heterocyclic ring, and wherein any of the rings may be optionally substituted by:

(a) one or more substituents independently selected from hydroxyl, halogen, —CN, —CO$_2$H, —CO$_2$(C$_1$–C$_6$)alkyl, —(C$_1$–C$_6$)alkyl-CO$_2$(C$_1$–C$_6$)alkyl, —CONH$_2$, —CONH(C$_1$–C$_6$)alkyl, —CON((C$_1$–C$_6$)alkyl)$_2$, —CHO, —CH$_2$OH, —(C$_1$–C$_4$)perfluoroalkyl, —O(C$_1$–C$_6$)alkyl, —S(C$_1$–C$_6$)alkyl, —SO(C$_1$–C$_6$)alkyl, —SO$_2$(C$_1$–C$_6$)alkyl, —NO$_2$, —NH$_2$, —NH(C$_1$–C$_6$)alkyl, —N((C$_1$–C$_6$)alkyl)$_2$, and —NHCO(C$_1$–C$_6$)alkyl, or (b) a group selected from (C$_1$–C$_6$)alkyl, (C$_2$–C$_6$)alkenyl, (C$_2$–C$_6$)alkynyl, (C$_3$–C$_8$)cycloalkyl, (C$_4$–C$_8$)cycloalkenyl, phenyl, benzyl, heteroaryl or heteroarylmethyl any of which groups may be optionally substituted with one or more substituents selected from halogen, hydroxyl, amino, carboxyl, (C$_1$–C$_4$)perfluoroalkyl, (C$_1$–C$_6$)alkyl, —O(C$_1$–C$_6$)alkyl or —S(C$_1$–C$_6$)alkyl;

R$_5$ is hydrogen or a (C$_1$–C$_6$)alkyl group;

or a salt, hydrate or solvate thereof.

As used herein the term "(C$_1$–C$_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, pentyl and hexyl.

The term "(C$_2$–C$_6$)alkenyl" means a straight or branched chain alkenyl moiety having from 2 to 6 carbon atoms and having in addition one double bond of either E or Z stereochemistry where applicable. This term would include, for example, vinyl, 1-propenyl, 1- and 2-butenyl and 2-methyl-2-propenyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 3–8 carbon atoms and includes, for example, cyclohexenyl, cyclooctenyl, cycloheptenyl, cyclopentenyl, cyclobutenyl and cyclopropenyl. In the case of cycloalkenyl rings of from 5–8 carbon atoms, the ring may contain more than one double bond.

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, dimidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3-methyl-2,5-dioxo-1-imidazolidinyl and 3,4,4-trimethyl-2,5-dioxo-1-imidazolidinyl, or (ii) a naphthalimido (i.e. 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

The term "5- or 6-membered heterocyclic ring" means such rings having 5 or 6 atoms in the ring, wherein the heteroatom(s) may be one or more nitrogen, oxygen or sulphur atoms, and includes heterocycles containing nitrogen, oxygen, or sulphur alone or containing two nitrogen atoms, a nitrogen and an oxygen atom, a nitrogen and a sulphur atom, two nitrogen atoms and an oxygen atom, two nitrogen atoms and a sulphur.

The "heteroaryl" means a 5–7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with up to four substituents, each of which independently may be (C$_1$–C$_6$)alkoxy, hydroxy, mercapto, (C$_1$–C$_6$)alkylthio, amino, halo (including fluoro, chloro, bromo andiodo), trifluoromethyl, nitro, —COOH, —CONH$_2$or —CONHR$^A$ wherein R$^A$ is a (C$_1$–C$_6$)alkyl group or the residue of a natural alpha-amino acid.

The term "characteristic side chain of a natural alpha-amino acid" means the characteristic side chain attached to the —CH(NH$_2$)(COOH) moiety in the following amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When R$_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. In this context, protected amino groups include amido and acylamino, protected hydroxy or mercapto groups include ethers and thioethers, protected carboxyl groups include esters, and imidazolyl, indolyl or guanidyl groups may be protected as t-butoxycarbonyl derivatives. These are only examples of the many protecting derivatives known in the art, and others will be known to the skilled man.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the R$_1$ and X groups —S,

C atom carrying the R$_2$ group —R,

C atom carrying the R$_3$ group —S, but mixtures in which the above configurations predominate are also contemplated.

As previously stated, the compounds of the invention are principally distinguished from the compounds disclosed in the prior art patent publications listed above by the identity of the group R$_4$. Accordingly, the groups R$_1$, R$_2$, R$_3$, and R$_5$ may be any of the groups which have been disclosed in the corresponding positions of compounds disclosed in any of those prior art patent publications listed above. Without limiting the generality of the foregoing, the following classes of substituent R$_3$ have been disclosed in the corresponding position of prior art compounds, and are therefore suitable R$_3$ groups for use in compounds of the present invention:

($C_1$-$C_6$)alkyl, benzyl, hydroxybenzyl, benzyloxybenzyl, ($C_1$-$C_6$)alkoxybenzyl, or benzyloxy($C_1$-$C_6$)alkyl group; and the characterising group of a natural α amino acid, in which any functional group may be protected, any amino group may be acylated and any carboxyl group present may be amidated; and a group —[Alk]$_n$R$_6$ where Alk is a ($C_1$-$C_6$)alkyl or ($C_2$-$C_6$)alkenyl group optionally interrupted by one or more —O—, or —S— atoms or —N(R$_7$)— groups [where R$_7$ is a hydrogen atom or a ($C_1$-$C_6$)alkyl group], n is 0 or 1, and R$_6$ is an optionally substituted cycloalkyl or cycloalkenyl group; and a benzyl group substituted in the phenyl ring by a group of formula —OCH$_2$COR$_8$ where R$_8$ is hydroxyl, amino, ($C_1$-$C_6$)alkoxy, phenyl($C_1$-$C_6$)alkoxy, ($C_1$-$C_6$) alkylamino, di(($C_1$-$C_6$)alkyl)amino, phenyl($C_1$-$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; and a heterocyclic(($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$)alkylamino, di-($C_1$-$C_6$)alkylamino, mercapto, ($C_1$-$C_6$)alkylthio, hydroxy($C_1$-$C_6$)alkyl, mercapto($C_1$-$C_6$)alkyl or ($C_1$-$C_6$)alkylphenylmethyl;

R$_3$ may also be a group —CR$_a$R$_b$R$_c$ in which:

each of R$_a$, R$_b$ and R$_c$ is independently hydrogen, ($C_1$-$C_6$)alkyl, ($C_2$-$C_6$)alkenyl, ($C_2$-$C_6$)alkynyl, phenyl($C_1$-$C_6$)alkyl, ($C_3$-$C_8$)cycloalkyl, the foregoing being subject to the proviso that R$_a$, R$_b$ and R$_c$ are not all hydrogen; or R$_c$ is hydrogen, ($C_1$-$C_6$)alkyl, ($C_2$-$C_6$)alkenyl, ($C_2$-$C_6$) alkynyl, phenyl($C_1$-$C_6$)alkyl, or ($C_3$-$C_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring (for example adamantyl); or R$_a$ and R$_b$ are each independently ($C_1$-$C_6$)alkyl, ($C_2$-$C_6$)alkenyl, ($C_2$-$C_6$)alkynyl, phenyl($C_1$-$C_6$) alkyl, or a group as defined for R$_c$ below other than hydrogen, or R$_a$ and R$_b$ together with the carbon atom to which they are attached form a 3 to 8 membered cycloalkyl or a 3- to 8-membered heterocyclic ring, and R$_c$ is hydrogen, —OH, —SH, halogen, —CN, —CO$_2$H, ($C_1$-$C_4$)perfluoroalkyl, —CH$_2$OH, —CO$_2$($C_1$-$C_6$)alkyl, —O($C_1$-$C_6$)alkyl, —O($C_2$-$C_6$)alkenyl, —S($C_1$-$C_6$)alkyl, —SO ($C_1$-$C_6$)alkyl, —SO$_2$($C_1$-$C_6$) alkyl, —S($C_2$-$C_6$) alkenyl, —SO($C_2$-$C_6$)alkenyl, —SO$_2$($C_2$-$C_6$) alkenyl or a group —Q—W wherein Q represents a bond or —O—, —S—, —SO— or —SO$_2$— and W represents a phenyl, phenylalkyl, ($C_3$-$C_8$)cycloalkyl, ($C_3$-$C_8$)cycloalkylalkyl, ($C_4$-$C_8$)cycloalkenyl, ($C_4$-$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$-$C_6$)alkyl, —CONH$_2$, —CONH($C_1$-$C_6$) alkyl, —CONH($C_1$-$C_6$alkyl)$_2$, —CHO, —CH$_2$OH, ($C_1$-$C_4$)perfluoroalkyl, —O($C_1$-$C_6$)alkyl, —S($C_1$-$C_6$)alkyl, —SO($C_1$-$C_6$)alkyl, —SO$_2$ ($C_1$-$C_6$)alkyl, —NO$_2$, —NH$_2$, —NH($C_1$-$C_6$)alkyl, —N(($C_1$-$C_6$)alkyl)$_2$, —NHCO($C_1$-$C_6$)alkyl, ($C_1$-$C_6$)alkyl, ($C_2$-$C_6$)alkenyl, ($C_2$-$C_6$)alkynyl, ($C_3$-$C_8$)cycloalkyl, ($C_4$-$C_8$)cycloalkenyl, phenyl or benzyl.

More specifically with respect to the groups R$_1$, R$_2$, R$_3$, R$_4$ and R$_5$ in compounds of the invention:

Examples of particular R$_1$ groups include hydrogen, methyl, ethyl, hydroxyl, allyl, thienylsulphanylmethyl, thienylsulphinylmethyl, thienylsulphonylmethyl and phthalimidomethyl. Presently preferred are compounds in which R$_1$ is hydrogen, hydroxyl, allyl or phthalimidomethyl.

Examples of particular R$_2$ groups include iso-butyl, n-pentyl, n-hexyl, n-heptyl, n-octyl, n-nonyl, n-decyl, cyclohexylpropyl, phenylpropyl, 4-chlorophenylpropyl, 4-methylphenylpropyl, 4-methoxyphenylpropyl, phenylbutyl, propyloxymethyl and propylsulphanyl. Presently preferred are compounds in which R$_2$ is isobutyl, n-heptyl, or phenylpropyl.

Examples of particular R$_3$ groups include benzyl, iso-butyl or t-butyl, 1-benzylthio-1-methylethyl, and 1-mercapto-1-methylethyl. Presently preferred are compounds in which R$_3$ is t-butyl or 1-mercapto-1-methylethyl.

Examples of R$_4$ groups include optionally substituted phenyl, napthyl, furanyl, thienyl, pyrrolinyl, tetrahydrofuranyl, imidazolyl, oxadiazolyl, thiazolyl, thiadiazolyl, pyridinyl, pyridinyl N-oxides, piperazinyl, indolyl, benzimidazolyl, benzotriazolyl, pyrazinyl, pyridazinyl, pyrimidinyl, dithianyl, benzo[b] thienyl, isoxazolyl or quinolinyl. Examples of particular R$_4$ groups include phenyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditrifluoromethylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, 2-napthyl, furan-2-yl, thien-2-yl, pyrrol-2-yl, tetrahydrofuran-2-yl, imidazol-2-yl, thiazol-2-yl, 4-ethoxycarbonylmethylthiazol-2-yl, 4-phenylthiazol-2-yl, 4,5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl , 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1, 2,4-thiadiazol-5-yl, 1,3,4-thiadiazol-2-yl, 5-methyl-1, 3,4-thiadiazol-2-yl, pyridin-2-yl, pyridin-3-yl, pyridin-4-yl, N-oxides of pyridin-2-yl pyridin-3-yl and pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl, quinolin-3-yl. In general, compounds wherein $R_4$ is a thiazolyl or substituted thiazolyl group are preferred for their activity in inhibiting the release of TNF. Presently preferred are compounds in which $R_4$ is phenyl, 3-methoxyphenyl, pyridin-2-yl, pyridin-3-yl, and thiazol-2-yl, 4,5-dimethylthiazol-2-yl, 5-bromothiazol-2-yl, 4-ethoxycarbonylmethylthiazol-2-yl, 5-methyl-1,3,4-thiadiazol-2-yl or 4-tertbutylthiazol-2-yl. Particularly preferred at present are compounds wherein $R_4$ is 3-methoxyphenyl, pyridin-2-yl, pyridin-3-yl, thiazol-2-yl, 4-ethoxycarbonylmethylthiazol-2-yl, 5-methyl-1,3,4-thiadiazol-2-yl and 4-tert-butylthiazol-2-yl.

Examples of particular $R_5$ groups include hydrogen, methyl and ethyl. Presently preferred are compounds in which $R_5$ is hydrogen.

Compounds of the present invention which are currently preferred for their combination of high intrinsic activity and good bioavailability when administered orally are:

3R-(2,2-Dimethyl-1S-pyridin-2-ylcarbamoyl-propylcarbamoyl)-5-methyl-2S-propen-2-yl-hexanohydroxamic acid, 3R-(2,2-Dimethyl-1S-pyridin-2-ylcarbamoyl-propylcarbamoyl)-2S-hydroxy-5-methylhexanohydroxamic acid, 3R-(2,2-Dimethyl-1S-(5-methylthiadiazol-2-ylcarbamoyl)-propylcarbamoyl)-2S-hydroxy-5-methylhexanohydroxamic acid, 3R-(2,2-Dimethyl-1S-(3-methoxyphenyl)carbamoyl-propylcarbamoyl)-2S-hydroxy-5-methylhexanohydroxamic acid, 3R-(2,2-Dimethyl-1S-pyrid-3-ylcarbamoyl-propylcarbamoyl)-2S-hydroxy-5-methylhexanohydroxamic acid and 3R-(2,2-Dimethyl-1S-pyridin-2-ylcarbamoyl-propylcarbamoyl)-5-methyl-2S-phthalimidomethylhexanohydroxamic acid, and salts, solvates or hydrates thereof.

Compounds of the present invention which are currently preferred for their activity in inhibiting TNF release are:

3R-(2,2-Dimethyl-1S-(thiazol-2-ylcarbamoyl)-propylcarbamoyl)-5-methyl-2S-propen-2-yl-hexanohydroxamic acid, 3R-(2,2-Dimethyl-1S-(thiazol-2-ylcarbamoyl)-propylcarbamoyl)-2S-hydroxy-5-methylhexanohydroxamic acid, and 3R-(2,2-Dimethyl-1S-(4-ethoxycarbonylmethylthiazol-2-ylcarbamoyl)propylcarbamoyl)-2S-hydroxy-5-methylhexanohydroxamic acid, and salts, solvates or hydrates thereof.

Further specific compounds of the invention are:

$N^1$-[2,2-Dimethyl-1S-(pyridin-2-ylcarbamoyl)-propyl]-$N^4$-hydroxy-2R-isobutyl-3S-methoxy-succinamide 5-Methyl-3R-(2-phenyl-1S-phenylcarbamoyl-ethylcarbamoyl)hexanohydroxamic acid, 3R-(2,2-Dimethyl-1S-phenylcarbamoyl-propylcarbamoyl)-5-methylhexanohydroxamic acid, 3R-(2,2-Dimethyl-1S-pyridin-2-ylcarbamoyl-propylcarbamoyl)-5-methylhexanohydroxamic acid, 3R-(2,2-Dimethyl-1S-phenylcarbamoyl-propylcarbamoyl)-2S-hydroxy-5-methylhexanohydroxamic acid, 2S-Hydroxy-3R-(3-methyl-1S-napth-2-ylcarbamoyl-butylcarbamoyl)-5-methylhexanohydroxamic acid 2S-Hydroxy-3R-(3-methyl-1S-(4-methoxyphenyl)carbamoyl-butylcarbamoyl)-5-methyl-hexanohydroxamic acid, 3R-(2,2-Dimethyl-1S-(4-tertbutyl-2,6-dimethylpylcarbamoyl)carbamoylpropylcarbamoyl)-2S-hydroxy-5-methylhexanohydroxamic acid, 3R-(2,2-Dimethyl-1S-(4-methoxyphenyl)carbamoyl-propylcarbamoyl)-2S-hydroxy-5-methylhexanohydroxamic acid, 3R-(2,2-Dimethyl-1S-pyrid-4-ylcarbamoyl-propylcarbamoyl)-2S-hydroxy-5-methylhexanohydroxamic acid, 3R-(2,2-Dimethyl-1S-(4-hydroxyphenyl)carbamoyl-propylcarbamoyl)-2S-hydroxy-5-methylhexanohydroxamic acid, 3R-(2-Benzylthio-2-methyl-1S-(pydin-2-ylcarbamoyl)propylcarbamoyl)-2S-hydroxy-5-methylhexanohydroxamic acid, 3R-(2,2-Dimethyl-1S-phenylcarbamoyl-propylcarbamoyl)-2S-hydroxy-5-phenylhexanohydroxamic acid 3R-(2,2-Dimethyl-1S-(4,5-dimethylthiazol-2-ylcarbamoyl)-propylcarbamoyl)-2S-hydroxy-5-methylhexanohydroxamic acid, 3R-(2,2-Dimethyl-1S-(5-bromo-thiazol-2-ylcarbamoyl)-propylcarbamoyl)-2S-hydroxy-5-methylhexanohydroxamic acid, 3R-(2,2-Dimethyl-1S-(4-phenyl-thiazol-2-ylcarbamoyl)-propylcarbamoyl)-2S-hydroxy-5-methylhexanohydroxamic acid, 3R-(2,2-Dimethyl-1S-(4-tert-butylthiadiazol-2-ylcarbamoyl)-propylcarbamoyl)-2S-hydroxy-5-methylhexanohydroxamic acid, 3R-(2,2-Dimethyl-1S-phenylcarbamoyl-propylcarbamoyl)-5-methyl-2S-propen-2-yl-hexanohydroxamic acid, 3R-(2,2-Dimethyl-1S-(4-methoxyphenylcarbamoyl)-propylcarbamoyl)-5-methyl-2S-propen-2-yl-hexanohydroxamic acid, 3R-(2-Benzylthio-2-methyl-1S-(pyridin-2-ylcarbamoyl)-propylcarbamoyl)-5-methyl-2S-propen-2-yl-hexanohydroxamic acid, 3R-(2,2-Dimethyl-1S-(pyridin-3-ylcarbamoyl)-propylcarbamoyl)-5-methyl-2S-propen-2-yl-hexanohydroxamic acid, 3R-(2,2-Dimethyl-1S-(4-hydroxyphenylcarbamoyl)-propylcarbamoyl)-5-methyl-2S-propen-2-yl-hexanohydroxamic acid, 3R-(2,2-Dimethyl-1S-(3-methoxyphenylcarbamoyl)-propylcarbamoyl)-5-methyl-2S-propen-2-yl-hexanohydroxamic acid, 3R-(2,2-Dimethyl-1S-(pyridin-4-ylcarbamoyl)-propylcarbamoyl)-5-methyl-2S-propen-2-yl-hexanohydroxamic acid, 3R-(2,2-Dimethyl-1S-(2-methoxyphenylcarbamoyl)-propylcarbamoyl)-5-methyl-2S-thien-2-ylsulfanylmethyl-hexanohydroxamic acid, 3R-(2,2-Dimethyl-1S-(pyridin-2-ylcarbamoyl)-propylcarbamoyl)-5-methyl-2S-thien-2-ylsulfanylmethyl-hexanohydroxamic acid, 3R-(2,2-Dimethyl-1S-(2-methoxyphenylcarbamoyl)-propylcarbamoyl)-5-methyl-2S-thien-2-ylsulfinylmethyl-hexanohydroxamic acid, 3R-(2.2-Dimethyl-1S-(pyridin-2-ylcarbamoyl)-
propylcarbamoyl)-5-methyl-2S-thien-2-ylsulfinylmethyl-
hexanohydroxamic acid.

3R-(2.2-Dimethyl-1S-phenylcarbamoyl-propylcarbamoyl)-
2S-hydroxy-5-phenylhexanoic acid.

3R-(2.2-Dimethyl-1S-(N-oxy-pyridin-2-yl)carbamoyl-
propylcarbamoyl)-2S-hydroxy-5-
methylhexanohydroxamic acid.

and salts, solvates or hydrates thereof.

Compounds according to the present invention in which X is a hydroxamic acid group —CONHOH may be prepared from corresponding compounds of the invention in which X is a carboxylic acid group —COOH or from the corresponding protected hydroxamic acid derivatives. That process, which forms another aspect of the invention, comprises:

(a) causing an acid of general formula (II)

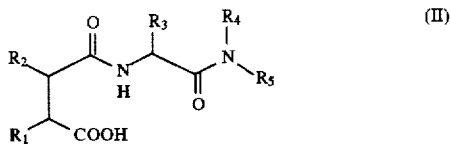

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$; or (b) deprotecting a diprotected hydroxamic acid derivative of formula (IIb)

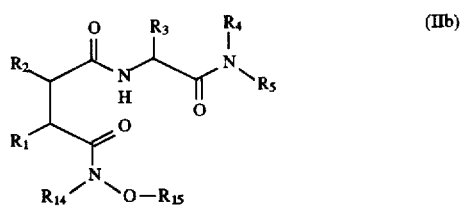

in which $R_1$, $R_2$, $R_3$, $R_4$, and $R_5$ are as defined in general formula (I), $R_{14}$ is an amino protecting group and $R_{15}$ is a hydroxyl protecting group.

For method (a) conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyidimethylsilylhydroxylamine, N-tert-butoxycarbonyl-O-tetrahydropyranylhydroxylamine, and N,O-bis(tert-butoxycarbonyl)hydroxylamine.

For method (b) suitable protecting groups $R_{14}$ and $R_{15}$ are benzyl and substituted benzyl (e.g. 4-methoxybenzyl). Such protecting groups may be removed by hydrogenolysis, while the 4-methoxybenzyl group may also be removed by acid hydrolysis.

In method (a) in the special case where $R_1$ in compound (I) is hydroxy, a particularly useful technique may be reaction of hydroxylamine with a dioxalone of formula (IIa):

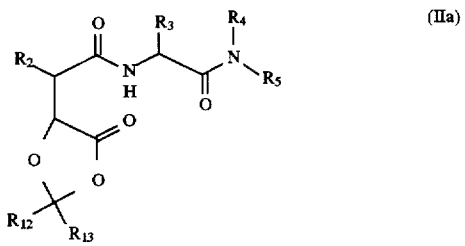

wherein the groups $R_{12}$ and $R_{13}$ are derived from a dioxalone forming reagent, and may be, for example, hydrogen, alkyl, phenyl or substituted phenyl. The dioxalone ring is opened on reaction with hydroxylamine to give the required hydroxamic acid derivative of formula (I).

Compounds according to the present invention in which X is a carboxylic acid group —COOH may be prepared by a process comprising: coupling an acid of formula (III) or an activated derivative thereof with an amine of formula (IV)

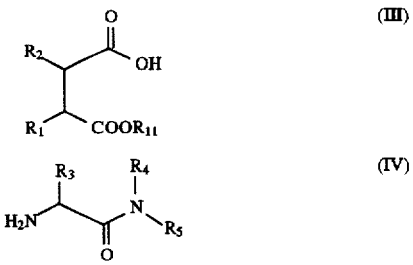

wherein $R_1$ $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$ $R_2$, $R_3$, $R_4$, and $R_5$.

Compounds of formula (IIb) may be prepared by a process comprising: causing an acid of formula (IIIa) or an activated derivative thereof to react with an amine of formula (IV)

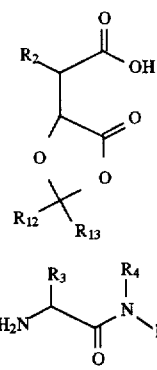

(IIIa)

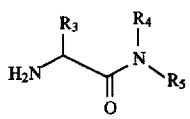

(IV)

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, $R_{14}$ is an amino protecting group and $R_{15}$ is a hydroxyl protecting group as referred to in connection with formula (IIb) above, and subsequently removing any protecting groups from $R_1$ $R_2$, $R_3$, $R_4$, and $R_5$.

Active derivatives of acids (III) and (IIa) include activated esters such as the pentafluorophenyl ester, acid anhydrides and acid halides, e.g. chlorides. Suitable hydroxy protecting groups $R_{11}$ may be selected from those known in the art.

Amine intermediates of formula (IV) are either known compounds or may be prepared from known amino acid starting materials using standard methods and by analogy with the specific preparative examples herein.

In the special case where $R_1$ in compound (III) or (IIIa) is hydroxy, it too may be protected during the coupling of compounds (III) or (IIIa) and (IV). In the case where $R_1$ is hydroxy in compound (III) a particularly useful technique may be simultaneous protection of the two hydroxy groups as a dioxalone of formula (V):

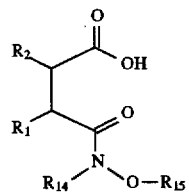

(V)

wherein the groups $R_{12}$ and $R_{13}$ are derived from a dioxalone forming reagent, and may be, for example, hydrogen, alkyl, phenyl or substituted phenyl.

As mentioned above, compounds of formula (I) are useful in human or veterinary medicine since they are active as inhibitors of MMPs, and a further advantage lies in their ability to inhibit the release of tumour necrosis factor (TNF) from cells.

A compound of the present invention which is currently preferred for it's combination of high intrinsic activity and good bioavailability when administered orally, and for its activity in animal models of neurodegenerative disease, especially multiple sclerosis is $N^1$-[2,2-dimethyl-1S-(pyridin-2-ylcarbamoyl)-propyl]-$N^4$-hydroxy-2R-isobutyl-3S-methoxy-succinamide.

Accordingly in another aspect, this invention concerns:

(i) a method of management (by which is meant treatment or prophylaxis) of diseases or conditions mediated by MMPs and/or TNF in mammals, in particular in humans, which method comprises administering to the mammal an effective amount of a compound as defined with respect to formula (I) above, or a pharmaceutically acceptable salt thereof; and (ii) a compound as defined with respect to formula (I) for use in human or veterinary medicine, particularly in the management (by which is meant treatment or prophylaxis) of diseases or conditions mediated by MMPs and/or TNF; and (iii) the use of a compound as defined with respect to formula (I) in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory and neuroinflammatory diseases, dermatological conditions, solid tumour growth and tumour invasion by secondary metastases, and angiogenesis dependent diseases, in particular rheumatoid arthritis, osteoarthritis, periodontitis, gingivitis, corneal ulceration, solid tumour growth and tumour invasion by secondary metastases, neovascular glaucoma, multiple sclerosis, and psoriasis. Diseases or conditions mediated by TNF include inflammation, fever, cardiovascular effects, haemorrhage, coagulation and acute phase response, cachexia and anorexia, acute infections, shock states, graft versus host reactions and autoimmune disease.

The invention in one of its preferred aspects also includes a method for the management of multiple sclerosis in mammals, including humans, comprising administering to the mammal an amount of $N^1$-[2,2-dimethyl-1S-(pyridin-2-ylcarbamoyl)-propyl]-$N^4$-hydroxy-2R-isobutyl-3S-methoxy-succinamide effective to reduce the symptomatic and/or pathological manifestations of multiple sclerosis.

In a further aspect of the invention there is provided a pharmaceutical or veterinary composition comprising a compound of formula (I) together with a pharmaceutically or veterinarily acceptable excipient or carrier. Included within this aspect of the invention is a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycalene, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The following Examples illustrate embodiments of the invention:

The amino acids used in the examples were commercially available or were prepared according to literature procedures.

The following abbreviations have been used throughout:

| DIPE | Diisopropyl ether |
| DMF | N,N-Dimethylformamide |
| HOBt | 1-Hydroxybenzotriazole |
| LDA | Lithium diisopropylamide |
| mCPBA | m-Chloroperbenzoic acid |
| NMM | N-Methylmorpholine |
| THF | Tetrahydrofuran |
| TFA | Trifluoroacetic acid |
| TLC | Thin layer chromatography |
| EDC | N-Ethyl-N'-(3-dimethylaminopropyl)carbodiimide hydrochloride |

$^1$H and $^{13}$C NMR spectra were recorded using a Bruker AC 250E spectrometer at 250.1 and 62.9 MHz, respectively. Elemental microanalyses were performed by CHN Analysis Ltd. (Alpha House, Countesthorpe Road, South Wigston, Leicester LE8 2PJ, UK) or Medac Ltd. (Department of Chemistry, Brunel University, Uxbridge, Middlesex UB8 3PH).

EXAMPLE 1

5-Methyl-3R-(2-phenyl-1S-phenylcarbamoyl-ethylcarbamoyl)-hexanohydroxamic acid

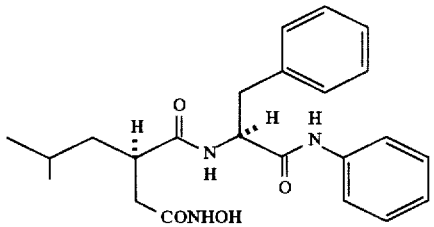

STEP A

N-(4-Methylpentanoyl)-4S-phenylmethyl-oxazolidin-2-one

A dry 500 ml flask equipped with a magnetic stirrer was charged with 4S-phenylmethyl-oxazolidin-2-one (17.72 g, 100 mmol), this was capped with a rubber septum and flushed with nitrogen. Anhydrous THF (300 ml) was added via a cannula and the resulting solution was cooled to −78° C. in an acetone/dry-ice bath. A solution of 1.47M n-butyllithium in hexane (68.4 ml, 101 mmol) was transferred via cannula to a dry, septum-stoppered 100 ml dropping funnel. This was added dropwise to the THF solution over 10 minutes.

4-Methylvaleric acid chloride (14.80 g, 110 mmol) was added in one portion by syringe after completion of the addition of n-butyllithium. The resulting solution was stirred at −78° C. for 30 minutes and then allowed to warm to ambient temperature over 30 minutes. Excess acid chloride was quenched by the addition of aq. ammonium chloride (60 ml) and the bulk of the solvent was removed under reduced pressure. The resulting slurry was extracted with dichloromethane (2×80 ml). The combined organic extracts were washed with 1M sodium hydroxide (75 ml), brine (75 ml), dried (anhydrous sodium sulphate) and filtered. The solvent was removed to yield a yellow oil (29.20 g, including residual solvent) which was used directly in Step B. $^1$H-NMR; δ (CDCl$_3$), 7.34–7.19 (5H, m), 4.73–4.63 (1H, m), 4.25–4.16 (2H, m), 3.30 (1H, dd, J=3.3 Hz), 3.05–2.85 (2H, m), 2.78 (1H, dd, J=9.5 Hz), 1.76–1.53 (3H, m) and 0.97 (6H, d, J=6.2 Hz).

STEP B

N-(4-(tert-Butyl)-2R-isobutyl-butan-1,4-dioyl)-4S-phenylmethyl-oxazolidin-2-one

N-(4-Methylpentanoyl)-4S-phenylmethyl-oxazolidin-2-one (20 g, 72.6 mmol) was placed in a dry 1 liter 3-necked flask to which was added dry THF (400 ml). The mixture was kept under a stream of argon and cooled to −78° C. (dry ice/acetone). Sodium bis(trimethyl)silylamide (1M solution in THF, 72.6 ml, 72.6 mmol) was added dropwise through a dropping funnel. After stirring for 20 minutes, tert-butyl bromoacetate (21.02 g, 15.8 ml, 109 mmol) was added dropwise over 1 minute, to give an orange solution. The mixture was kept at −78° C. and allowed to warm to −50° C. over 2 hours (after which time it turned pink). The reaction was then quenched by adding acetic acid (10.90 g, 10.4 ml, 182 mmol) in ether (50 ml) at −50° C., whereupon the solution became colourless. The solvent was removed under reduced pressure and the resulting slurry was partitioned between ethyl acetate and brine. The ethyl acetate layer was washed once with brine and the original brine layer was back-extracted with ethyl acetate. The combined organic layers were dried and the solvent removed, giving a yellow oil which crystallised on cooling overnight to yield the title compound as a crystalline solid (21.36 g, 76%).

$^1$H-NMR; δ (CDCl$_3$), 7.38–7.24 (5H, m), 4.67 (1H, m), 4.27 (1H, m), 4.18–4.16 (2H, m), 3.36 (1H, dd, J=3.3 Hz), 2.72 (1H, dd, J=2.3 Hz), 2.49 (1H, dd, J=4.6 Hz), 1.72–1.24 (3H, m), 1.44 (9H, s) and 0.91–0.96 (6H, dd, J=4.5 Hz). $[α]^{25}_D$=+66.9.(c=1, MeOH).

STEP C

2R-Isobutyl-butan-1,4-dioic acid-4-tert-butyl ester

N-(4-(tert-Butyl)-2R-isobutyl-butan-1,4-dioyl)-4S-phenylmethyl-oxazolidin-2-one (15.30 g, 39 mmol) was placed in a 1 liter flask with a stirrer bar and to it was added a mixture of THF (600 ml) and water (150 ml). The solution was stirred and cooled to 0° C. (ice/acetone bath) then 60% aq. hydrogen peroxide (4.5 ml, 157 mmol) was added via syringe over 5 minutes, followed by lithium hydroxide (2.65 g, 63 mmol) in 100 ml water. The reaction mixture was stirred for 1 h at 0° C. TLC analysis (10% methanol in dichloromethane) showed complete reaction (product gave a yellow spot on TLC on staining with bromocresol green and heating). The reaction mixture was quenched with sodium nitrite (10.88 g, 157 mmol), the final pH was 12–13. THF was removed in-vacuo and the aqueous layer was extracted with dichloromethane (3×200 ml) to recover the chiral auxiliary. The organic extracts were dried (anhydrous magnesium sulphate), filtered and the solvent removed in-vacuo and the resulting solid chiral auxiliary (7.05 g, 39 mmol, 100%) recrystallised from ethyl acetate-hexane (2:1). $[α]^{25}_D$=–13.0° (c=1, MeOH)

The aqueous layer was cooled in an ice bath and acidified to pH 5–6 with 2M hydrochloric acid. The resulting cloudy solution was extracted with ethyl acetate (4×200 ml), readjusting the pH to 5–6 in between extractions. The combined organic extracts were dried over magnesium sulphate, filtered and the solvent was removed to yield the title compound as a pale yellow oil (8.21 g, 91%). $^1$H-NMR; δ (CDCl$_3$), 2.85 (1H, m), 2.59 (1H, dd, J=16, 9 Hz), 2.38 (1H, dd, J=16, 5 Hz), 1.64 (1H, m), 1.43 (9H, s), 1.28 (1H, m) and 0.93 (6H, dd, J=7, 8 Hz). $[α]^{25}_D$=+10.4.(c=1, MeOH)

STEP D

N$^α$-Benzyloxycarbonyl-L-phenylalanine-N-phenylamide

N$^α$-Benzyloxycarbonyl-L-phenylalanine (4.95 g, 16.5 mmol) was dissolved in dichloromethane (70 ml) and the solution was cooled to 0° C. and stirred during the addition of pentafluorophenol (3.35 g, 18.2 mmol), followed by EDC (3.49 g, 18.2 mmol). The mixture was allowed to warm to room temperature, stirred for a further 1 hour then cooled back to 0° C. Aniline (3.85 g, 41.4 mmol) was added dropwise and the mixture was warmed to room temperature then stirred overnight. The solution was washed twice with 1M sodium carbonate, twice with 1M hydrochloric acid and finally with brine before drying over anhydrous magnesium sulphate. The solution was filtered and evaporated to a white solid which was recrystallised from ethyl acetate-hexane. Yield: 2.57 g (41%). $^1$H-NMR; δ (CDCl$_3$), 7.87 (1H, br s), 7.43–7.03 (15H, br m), 5.62 (1H, m), 5.08 (2H, s), 4.59 (1H, s) and 3.15 (2H, s).

STEP E

L-Phenylalanine-N-phenylamide

N$^α$-Benzyloxycarbonyl-L-phenylalanine-N-phenylamide (2.50 g, 6.68 mmol) was dissolved in ethanol (20 ml) and cyclohexene (5 ml) and 10% palladium on charcoal (250 mg) was added. The mixture was heated at reflux for 1 hour after which time no starting material was detectable (as indicated by TLC analysis). The catalyst was removed by filtration and the solvent evaporated to leave the title compound contaminated with residual ethanol (1.74 g). $^1$H-NMR; d (CD$_3$OD), 7.45 (2H, m), 7.18 (7H, m), 7.04 (1H, m), 3.56 (1H, m), 3.04 (1H, dd, J=6.4, 13.3 Hz) and 2.85 (1H, dd, J=7.2, 13.3 Hz).

STEP F

5-Methyl-3R-(2-phenyl-1S-phenylcarbamoyl-ethylcarbamoyl)-hexanoic acid tert-butyl ester 2R-Isobutyl-butan-1,4-dioic acid-4-tert-butyl ester (1.17 g, 5.11 mmol), prepared according to the method described in STEP C, was dissolved in DMF (30 ml) and the solution was cooled in an ice bath. HOBt (0.76 g, 5.62 mmol) and EDC (1.07 g, 5.62 mmol) were added and the reaction mixture was stirred for 90 minutes at 0° C. and 30 minutes at room temperature. The mixture was cooled back to 0° C., L-phenylalanine-N-phenylamide (1.60 g, 6.65 mmol) was added and the reaction mixture was allowed to warm to room temperature with stirring overnight. TLC analysis indicated that all of the carboxylic acid precursor had been consumed. The solvent was removed and the residue was taken up in diethyl ether and washed successively with water, 1M sodium carbonate,1M hydrochloric acid and brine. The organic phase was dried (anhydrous magnesium sulphate), filtered and evaporated to leave an off-white solid. Recrystallisation from ethyl acetate-hexane afforded the title compound (1.23 g, 53%). $^1$H-NMR; δ (CDCl$_3$), 8.16 (1H, s), 7.39 (2H, m), 7.28 (7H, m), 7.08 (1H, m), 6.53 (1H, d, J=7.7 Hz), 4.82 (1H, dd, J=7.2, 14.5 Hz), 3.22 (2H, m), 2.66 (1H, m), 2.52 (1H, dd, J=8.6, 16.4 Hz), 2.37 (1H, dd, J=4.9, 16.4 Hz), 1.45 (2H, m), 1.43 (9H, s), 1.20 (1H, m), 0.86 (3H, d, J=6.4 Hz) and 0.81 (3H, d, J=6.2 Hz).

STEP G

5-Methyl-3R-(2-phenyl-1S-phenylcarbamoyl-ethylcarbamoyl)-hexanoic acid

5-Methyl-3R-(2-phenyl-1S-phenylcarbamoyl-ethylcarbamoyl)-hexanoic acid tert-butyl ester (1.22 g, 2.70 mmol) was dissolved in dichloromethane (7.5 ml) and TFA (7.5 ml) and the solution was stored overnight at 4° C. The solvents were removed in vacuo, the residue was dissolved in ethyl acetate and washed twice with water to remove residual TFA. The organic phase was dried (anhydrous magnesium sulphate), filtered and evaporated to leave a foam (1.07 g, including residual solvent). $^1$H-NMR; δ (CD$_3$OD), 7.41 (2H, m), 7.18 (7H, m), 7.02 (1H, m), 4.70 (1H, dd, J=7.0, 8.1 Hz), 3.17 (1H, dd, J=7.0, 13.7 Hz), 3.03 (1H, dd, J=8.1, 13.7 Hz), 2.76 (1H, m), 2.44 (1H, dd, J=8.4, 16.5 Hz), 2.28 (1H, dd, J=5.9, 16.5 Hz), 1.40 (2H, m), 1.21 (1H, m), 0.83 (3H, d, J=6.3 Hz) and 0.76 (3H, d, J=6.2 Hz).

STEP H

O-Benzyl-5-Methyl-3R-(2-phenyl-1S-phenylcarbamoyl-ethylcarbamoyl) hexanohydroxamate 5-Methyl-3R-(2-phenyl-1S-phenylcarbamoyl-ethylcarbamoyl)-hexanoic acid (1.00 g, 2.52 mmol) was dissolved in DMF (5 ml) and cooled to 0° C. in an ice bath. HOBt (0.41 g, 3.03 mmol), EDC (0.58 g, 3.03 mmol) and NMM were added and the mixture was stirred for 1 hour at 0° C. followed by a further 2 hours at room temperature. The reaction was cooled back to 0° C. during the addition of O-benzylhydroxylamine (0.47 g, 3.78 mmol) and then allowed to warm to room temperature with stirring overnight. The solvent was removed in vacuo to leave an oil which crystallised on stirring with diethyl ether and water. Trituration with ethyl acetate gave the required product (0.63 g, 50%) which was used in STEP I without further purification. $^1$H-NMR; δ (CD$_3$OD), 7.45 (2H, m), 7.38–7.08 (12H, m), 7.04 (1H, m), 4.76 (2H, m), 4.69 (1H, m), 3.19 (1H, dd, J=6.7, 13.8 Hz), 3.00 (1H, dd, J=8.6, 13.8 Hz), 2.75 (1H, m), 2.16 (1H, dd, J=8.0, 14.5 Hz), 2.02 (1H, dd, J=6.7, 14.5 Hz), 1.38 (2H, m), 1.18 (1H, m), 0.81 (3H, d, J=6.3 Hz) and 0.75 (3H, d, J=6.2 Hz).

STEP I

5-Methyl-3R-(2-phenyl-1S-phenylcarbamoyl-ethylcarbamoyl)-hexanohydroxamic acid

Hydrogen gas was bubbled through a slurry of O-benzyl-5-Methyl-3R-(2-phenyl-1S-phenylcarbamoyl-ethylcarbamoyl)-hexanohydroxamate (0.62 g, 1.23 mmol) and 10% palladium on charcoal (0.12 g) in ethanol (30 ml) for 90 minutes, after which time no starting material remained (as indicated by TLC analysis). The catalyst was removed by filtration and the filtrate was evaporated to leave a white solid. Recrystallisation from ethanol-ethyl acetate afforded the title compound (0.37 g, 73%). m.p. 183–184∞C. $^1$H-NMR; δ (CD$_3$OD), 7.45 (2H, m), 7.20 (7H, m), 7.05 (1H, m), 4.70 (1H, dd, J=7.0, 8.2 Hz), 3.17 (1H, dd, J=7.0, 13.7 Hz), 2.99 (1H, dd, J=8.3, 13.7 Hz), 2.76 (1H, m), 2.16 (1H, dd, J=7.4, 14.5 Hz), 2.04 (1H, dd, J=7.2, 14.5 Hz), 1.41 (2H, m), 1.08 (1H, m), 0.83 (3H, d, J=6.4 Hz) and 0.77 (3H, d, J=6.4 Hz). $^{13}$C-NMR; δ (CD$_3$OD), 177.3, 171.7, 170.6, 139.3, 138.5, 130.9, 129.7, 129.5, 127.7, 125.5, 121.8, 56.8, 42.5, 42.4, 39.0, 36.9, 26.9, 23.4 and 22.4. Found: C 65.64, H 6.96, N 9.91%; C$_{20}$H$_{31}$N$_3$O$_5$. 0.5H$_2$O requires: C 65.70H 7.19, N 9.99%.

The following additional compounds were prepared according to the methods of Example 1:

EXAMPLE 2

3R-(2,2-Dimethyl-1S-phenylcarbamoyl-propylcarbamoyl)-5-methylhexanohydroxamic acid

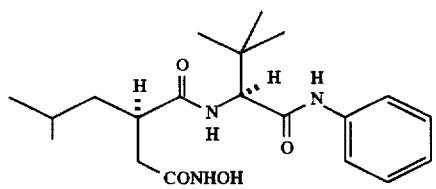

White powder. m.p. 151–153∞C. $^1$H-NMR; δ (CD$_3$OD), 7.48 (2H, d, J=7.8 Hz), 7.26 (2H, t, J=7.6 Hz), 7.05 (1H, t, J=7.3 Hz), 4.40 (1H, s), 2.95 (1H, m), 2.31 (1H, dd, J=7.8,14.6 Hz), 2.15 (1H, dd, J=6.6, 14.6 Hz), 1.51 (2H, m), 1.20 (1H, m), 1.03 (9H, s), 0.86 (3H, d, J=6.4 Hz) and 0.81 (3H, d, J=6.3 Hz). $^{13}$C-NMR; δ (CD$_3$OD), 177.2, 171.2, 170.6, 139.3, 129.8, 125.5, 121.6, 62.7, 42.5, 41.9, 37.1, 35.8, 27.2, 27.0, 23.5 and 22.6. Found: C 62.86, H 8.29, N 10.71%; C$_{20}$H$_{31}$N$_3$O$_4$·0.3 H$_2$O requires: C 62.74, H 8.32, N 10.97%

EXAMPLE 3

3R-(2,2-Dimethyl-1S-pyridin-2-ylcarbamoyl-propylcarbamoyl)-5-methylhexanohydroxamic acid

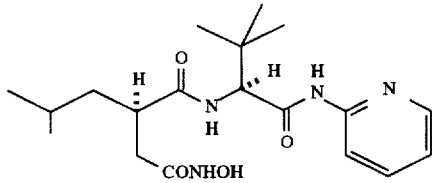

Pale grey solid. m.p. 125–126∞C. $^1$H-NMR; δ (CD$_3$OD), 8.26 (1H, m), 8.04 (1H d), 7.72 (1H, dt, J=1.9, 5.5 Hz), 7.07 (1H, m), 4.47 (1H, s), 2.97 (1H, m), 2.30 (1H, dd, J=7.8, 14.5 Hz), 2.18 (1H, dd, J=6.6, 14.5 Hz), 1.51 (2H, m), 1.15 (1H, m), 1.03 (9H, s), 0.86 (3H, d, J=6.5 Hz), and 0.80 (3H, d, J=6.4 Hz). $^{13}$C-NMR; δ (CD$_3$OD), 177.3, 171.6, 170.6, 152.6, 149.1, 139.5, 121.1, 115.7, 62.8, 42.5, 41.9, 37.0, 35.7, 27.2, 27.0, 23.5 and 22.5. Found: C 60.11, H 7.90, N 14.79%; C$_{19}$H$_{30}$N$_4$ O$_4$ requires: C 60.30, H 7.99, N 14.80%.

EXAMPLE 4

3R-(2,2-Dimethyl-1S-phenylcarbamoyl-propylcarbamoyl)-2S-hydroxy-5-methylhexanohydroxamic acid

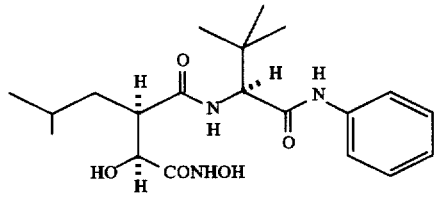

STEP A

2S-Hydroxy-3R-isobutenyl-butan-1,4-dioic acid diisopropyl ester

2S-Hydroxybutan-1,4-dioic acid diisopropyl ester (50 g, 230 mmol) was added to a solution of LDA [from N,N-diisopropylamine (80 ml, 570 mmol) and 10M n-butyllithium (48.1 ml, 481 mmol)] in dry THF (500 ml) whilst maintaining the temperature at −70° C. When addition was complete the reaction was warmed to −15° C. and stirred for 8 hours. The reaction mixture was cooled to −70° C. and methallyl iodide (46 g, 252 mmol) was added slowly, ensuring that the temperature did not exceed −65° C. The mixture was warmed to −40° C. and stirred for 18 hours before quenching at −15° C. with citric acid. The organic layer was separated and washed with 10% sodium hydrogen carbonate solution (500 ml) and brine (300 ml) then dried (anhydrous magnesium sulphate). The solution was filtered and concentrated in vacuo to give a brown oil (64 g) which was purified by column chromatography (silica gel, 1 kg, gradient elution with 20 to 35% diethyl ether in hexane). The desired product was isolated as a colourless oil (30.9 g, 49%) which was found to be a 17:1 mixture of diastereoisomers by NMR. $^1$H-NMR; δ (CDCl$_3$, major diastereoisomer), 5.06 (1H, septet, J=6.3 Hz), 4.97 (1H, septet, J=6.3 Hz), 4.78 (2H, d, J=7.1 Hz), 4.16 (1H, m), 3.20 (1H, d, J=6.2 Hz), 3.00 (1H, m), 2.50 (1H, dd, J=7.0, 14.5 Hz), 2.35 (1H, dd, J=8.7, 14.4 Hz), 1.72 (3H, s) and 1.24–1.16 (12H, 2m).

STEP B

2S-Hydroxy-3R-isobutyl-butan-1,4-dioic acid diisopropyl ester

2S-Hydroxy-3R-isobutenyl-butan-1,4-dioic acid diisopropyl ester (7.14 g, 26.2 mmol) was dissolved in ethanol (80 ml), and stirred overnight with 10% palladium on charcoal catalyst (1.0 g) under an atmosphere of hydrogen. The catalyst was removed by filtration and the filtrate was evaporated to dryness to leave the product as a clear oil (7.03 g, 98%). $^1$H-NMR; δ (CDCl$_3$), 5.06 (1H, septet, J=6.3 Hz), 4.97 (1H, septet, J=6.3 Hz), 4.17 (1H, br s,), 3.24 (1H, br s), 2.83 (1H, m), 1.68 (2H, m), 1.44 (1H, m), 1.24 (6H, d, J=6.2 Hz), 1.18 (6H, d, J=6.2 Hz) and 0.89 (6H, m).

STEP C

2S-Hydroxy-3R-isobutyl-butan-1,4-dioic acid

2S-Hydroxy-3R-isobutyl-butan-1,4-dioic acid diisopropyl ester (7.0 g, 25.6 mmol) was dissolved in dioxane (15 ml) and water (15 ml), a solution of potassium hydroxide (4.29 g) in water (22 ml) was added and the mixture was heated at 90° C. overnight. The solution was allowed to cool and then passed through an ion exchange resin (Dowex 50X4-400, 200 ml) and evaporated to yield the title compound (4.82 g, 99%). $^1$H-NMR; δ (CDCl$_3$), 8.70 (2H, br s), 4.32 (1H, br s), 3.10 (1H, m), 1.85–1.55 (3H, m) and 0.96 (6H, m).

STEP D

2R-(2,2-Dimethyl-4-oxo-1,3-dioxalan-5S-yl)-4-methylpentanoic acid

2S-Hydroxy-3R-isobutyl-butan-1,4-dioic acid (5.19 g, 27.3 mmol) was dissolved in 2,2-dimethoxypropane (150 ml) and DMF (40 ml) and stirred overnight at 30° C. in the presence of a catalytic amount of p-toluene sulphonic acid. The solvent was removed to give the title compound contaminated with solvent (6.87 g, crude). $^1$H-NMR; δ (CDCl$_3$), 4.41 (1H, d, J=4.8 Hz), 2.91 (1H, m), 1.69 (3H, m), 1.54 (3H, s), 1.48 (3H, s) and 0.88 (6H, m).

STEP E

2R-(2,2-Dimethyl-4-oxo-1,3-dioxalan-5S-yl)-4-methyl pentanoic acid pentafluorophenyl ester 2R-(2,2-Dimethyl-4-oxo-1,3-dioxalan-5S-yl)-4-methylpentanoic acid (558 mg, 2.4 mmol) was taken up in dichloromethane (10 ml) and cooled to 0° C. before adding pentafluorophenol (670 mg, 3.6 mmol) and EDC (560 mg, 2.9 mmol). The reaction was stirred at 0° C. for 2 hours then the solution was washed with 1M sodium carbonate (50 ml) and brine (20 ml). The organic layer was dried (magnesium sulphate), filtered, evaporated to dryness and purified by column chromatography (silica gel, dichloromethane) to give the activated ester (552 mg, 58%). $^1$H-NMR; δ (CDCl$_3$), 4.57 (1H, d, J=6.5 Hz), 3.32 (1H, m), 1.86 (3H, m), 1.67 (3H, s), 1.58 (3H, s) and 1.03 (6H, m).

STEP F

L-tert-leucine-N-phenylamide

The title compound was prepared from N-benzyloxycarbonyl-L-tert-leucine by methods analogous to those described in Example 1 (STEPS D and E). $^1$H-NMR; δ (CDCl$_3$), 7.53 (2H, m), 7.28 (2H, m), 7.06 (1H, m), 3.13 (1H, s) and 1.00 (9H, s).

STEP G

N$^2$-[2R-(2,2-Dimethyl-4-oxo-1,3-dioxalan-5S-yl)-4-methylpentanoyl]-L-tert-leucine-N-phenylamide 2R-(2,2-Dimethyl-4-oxo-1,3-dioxalan-5S-yl)-4-methylpentanoic acid pentafluorophenyl ester (1.72 g, 5.77 mmol) and L-tert-leucine-N-phenylamide (1.25 g, 6.06 mmol) were dissolved in DMF (150 ml) and the mixture was stirred-overnight at room temperature. The solvent was removed to give an oil which dissolved in diethyl ether and the solution was washed twice with 1M sodium carbonate and then with brine. The organic phase was dried (anhydrous magnesium sulphate), filtered and evaporated to an oil. Crystallisation from ethyl acetate-hexane afforded the desired product as a white solid (1.55 g, 64%). $^1$H-NMR; δ (CDCl$_3$), 8.53 (1H, s), 7.49 (2H, m), 7.26 (2H, m), 7.09 (1H, m), 7.00 (1H, d), 4.58 (1H, d), 4.52 (1H, d), 2.84 (1H, m), 1.78–1.47 (3H, br m), 1.64 (3H, s), 1.54 (3H, s), 1.09 (9H, s), 0.88 (3H, d, J=5.9 Hz) and 0.83 (3H, d, J=6.0 Hz).

STEP H

3R-(2,2-Dimethyl-1S-phenylcarbamoyl-propylcarbamoyl)-2S-hydroxy-5-methyl-1-hexanohydroxamic acid To a solution of hydroxylamine hydrochloride (0.93 g, 13.36 mmol) in methanol (10 ml) was added sodium methoxide (0.72 g, 13.36 mmol) and the mixture was stirred at room temperature for 2 hours, after which time the precipitated solid was removed by filtration. The filtrate was cooled in an ice bath prior to the addition of N$^2$-[2R-(2,2-dimethyl-4-oxo-1,3-dioxalan-5S-yl)-4-methylpentanoyl]-L-tert-leucine-N-phenylamide (1.40 g, 3.34 mmol) which was added in portions. The mixture was stirred at 0° C. for 10 minutes then allowed to warm to room temperature and stirred overnight. The solvent was removed under reduced pressure and the residue was purified by column chromatography (acid washed silica, 5% methanol in dichloromethane) followed by crystallisation from ethyl acetate-hexane. Yield: 0.89 g (68%). m.p. 122–1247∞C. $^1$H-NMR; δ (CD$_3$OD), 7.51 (2H, d, J=7.8 Hz) 7.27 (2H, m), 7.06 (1H, m), 4.40 (1H, s), 4.02 (1H, d, J=6.1 Hz), 2.86 (1H, m), 1.64 (1H, m), 1.51 (1H, m), 1.26 (1H, m), 1.03 (9H, s), 0.89 (3H, d, J=6.4 Hz), and 0.84 (3H, d, J=6.4 Hz). $^{13}$C-NMR; δ ((CD$_3$)$_2$SO), 172.6, 169.2, 168.8, 138.7, 128.6, 123.3, 119.3, 71.4, 60.5, 147.7, 37.3, 34.5, 26.6, 25.3, 23.5 and 21.8. Found: C 60.08, H 7.97, N 10.44% ; C$_{20}$H$_{31}$N$_3$O$_5$.0.4 H$_2$O requires: C 59.95, H 8.00, N 10.49%.

The following additional compounds were prepared according to the methods of Example 4:

EXAMPLE 5

2S-Hydroxy-3R-(3-methyl-1S-napth-2-ylcarbamoyl-butylcarbamoyl)-5-methylhexanohydroxamic acid

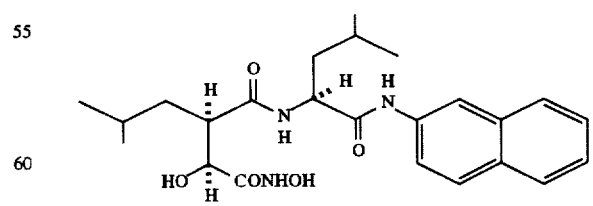

Off-white crystalline solid. m.p. 186∞C. $^1$H-NMR; δ (CD$_3$OD), 8.24 (0.5H, d, J=7.8 Hz), 8.15 (1H, s), 7.80–7.64 (3H, m), 7.54 (1H, br d, J=7.4 Hz), 7.43–7.29 (2H, m), 4.70–4.50 (1H, m), 4.03 (1H, d, J=6.8 Hz), 2.90–2.74 (1H, m), 1.83–1.41 (5H, m), 1.27–1.10 (1H, m), 0.95 (3H, d, J=5.2 Hz), 0.93 (3H, d, J=5.4 Hz), 0.89 (3H, d, J=6.4 Hz), and 0.82 (3H, d, J=6.4 Hz). $^{13}$C-NMR; δ (CD$_3$OD), 176.0, 173.3, 171.5, 161.7, 136.9, 135.1, 132.1, 129.5, 128.5, 127.4, 126.0, 121.4, 118.2, 73.1, 54.1, 54.0, 41.8, 39.1, 26.9, 25.8, 23.8, 23.6, 22.2 and 22.0. IR; ν$_{max}$ (KBr), 3422, 2917, 2850, 2363 and 1636.

EXAMPLE 6

2S-Hydroxy-3R-(3-methyl-1S-(4-methoxyphenyl) carbamoyl-butylcarbamoyl)-5-methylhexanohydroxamic acid

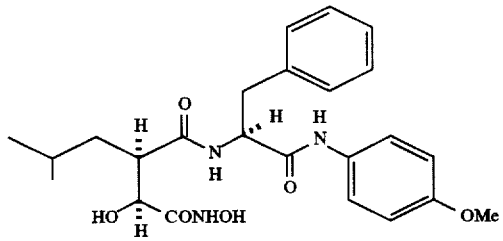

White powder. m.p. 192∞C. $^1$H-NMR; δ (CD$_3$OD), 7.33 (2H, d, J=8.8 Hz), 7.30–7.10 (5H, m), 6.80 (2H, d, J=8.8 Hz), 4.67 (1H, br dd 7.4, J=7.3 Hz), 4.01 (1H, d, J=5.9 Hz), 3.72 (3H, s), 3.19 (1H, dd, J=6.3, 13.6 Hz), 3.02 (1H, dd, J=8.1, 13.9 Hz), 2.79–2.60 (1H, m), 1.58–1.40 (1H, m), 1.40–1.19 (1H, m), 1.20–1.06 (1H, m), 0.80 (3H, d, J=6.5 Hz) and 0.77 (3H, d, J=6.6 Hz). $^{13}$C-NMR; δ (CD$_3$OD), 175.6, 171.5, 158.2, 138.4, 132.1, 130.4, 129.5, 127.8, 123.6, 114.8, 72.9, 56.7, 55.8, 39.2, 39.0, 26.7, 23.8 and 22.1. IR; ν$_{max}$ (KBr), 3420, 2343, 1653 and 1636 cm$^{-1}$.

EXAMPLE 7

3R-(2,2-Dimethyl-1S-(4-tertbutyl-2,6-dimethylphenyl)carbamoyl-propylcarbamoyl)-2S-hydroxy-5-methylhexanohydroxamic acid

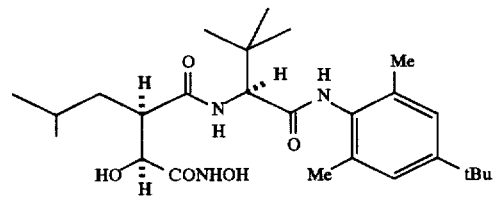

White solid. m.p. 209–210∞C. $^1$H-NMR; δ (CD$_3$OD), 7.07 (2H, s), 4.53 (1H, s), 3.98 (1H, d, J=7.2 Hz), 2.87 (1H, m), 2.16 (6H, s), 1.64 (1H, m), 1.51 (1H, m), 1.25 (9H, s), 1.16 (1H, m), 1.10 (9H, s), and 0.87 (6H, m). $^{13}$C-NMR; δ (CD$_3$OD), 175.5, 171.8, 171.7, 151.4, 136.2, 132.7, 126.2, 73.3, 62.1, 39.4, 35.6, 35.1, 31.7, 27.4, 26.9, 24.0, 22.2 and 19.3. Found: C 64.23, H 8.91, N 8.69%; C$_{26}$H$_{43}$N$_3$O$_5$. 0.5 H$_2$O requires: C 64.17, H 9.11, N 8.63%.

EXAMPLE 8

3R-(2,2-Dimethyl-1S-pyridin-2-ylcarbamoyl-propylcarbamoyl)-2S-hydroxy-5-methylhexanohydroxamic acid

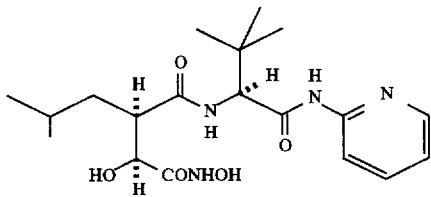

White powder. m.p. 132.5°–134.5° C. $^1$H NMR; δ (CDCl$_3$), 9.97 (1H, s), 9.52 (1H, s), 8.73 (1H, d, J=11.0 Hz), 8.18 (2H, m), 7.81 (1H, m), 7.13 (1H, m), 4.78 (1H, d, J=10.9 Hz), 4.19 (1H, m), 2.95 (1H, m), 2.00 (1H, m), 1.53 (1H, m), 1.42 (1H, m), 1.10 (9H, s), 0.86 (3H, d, J=6.2 Hz) and 0.85 (3H, d, J=6.1 Hz). $^{13}$C NMR; δ (CDCl$_3$), 174.4, 170.1, 169.0, 152.0, 146.3, 139.9, 120.1, 116.2, 73.8, 63.2, 42.0, 39.8, 34.8, 27.0, 25.8, 23.0 and 21.8. Found: C 57.33, H 7.53, N 13.84%; C$_{26}$H$_{43}$N$_3$O$_5$.0.2 H$_2$O requires: C 57.33, H 7.70, N 14.07%.

EXAMPLE 9

3R-(2,2-Dimethyl-1S-(4-methoxyphenyl)carbamoyl-propylcarbamoyl)-2S-hydroxy-5-methylhexanohydroxamic acid

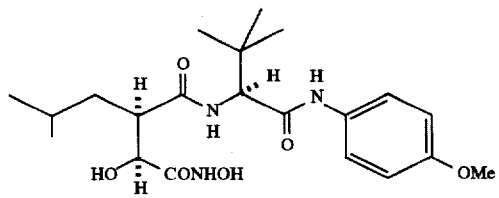

Pale brown solid. m.p. 118°–120° C. $^1$H NMR; δ (CD$_3$OD), 7.39 (2H, d, J=9.4 Hz), 6.81 (2H, d, J=9.4 Hz), 4.37 (1H, s), 4.15 (1H, d, J=6.9 Hz), 3.73 (3H, s), 2.91–2.79 (IH, m), 1.70–1.44 (2H, m), 1.33–1.13 (1H, m), 1.03 (9H, s), 0.89 (3H, d, J=6.3 Hz), and 0.85 (3H, d, J=6.3 Hz). $^{13}$C NMR; δ (CD$_3$OD), 175.6, 171.5, 171.0, 158.2, 132.1, 123.6, 115.0, 73.1, 62.4, 55.9, 39.7, 35.9, 30.9, 27.2, 27.0, 23.6 and 22.4. IR. ν$_{max}$(KBr) 3419, 2923, 2361, 1654, 1512, 1458, 1245, 1036 cm$^{-1}$. Found: C 57.97%, H 7.73%, N 9.31%; C$_{21}$H$_{33}$N$_3$O$_6$.0.6 H$_2$O requires C 58.08%, H 7.94%, N 9.67%.

EXAMPLE 10

3R-(2,2-Dimethyl-1S-pyrid-4-ylcarbamoyl-propylcarbamoyl)-2S-hydroxy-5-methylhexanohydroxamic acid

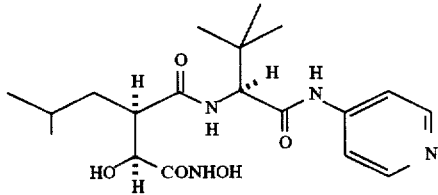

White solid. m.p 120°–125° C. $^1$H-NMR; δ ((CD$_3$)$_2$SO, 9:1 mixture of diastereoisomers), 10.62 (1H, s), 10.59 (0.9H, s), 10.43 (0.1H, s), 8.40 (2H, d, J=6.2 Hz), 7.80 (0.9H, d, J=8.6 Hz), 7.76 (0.1H, d, J=6.3 Hz), 7.60 (2H, d, J=6.2 Hz), 5.60 (0.1H, s), 5.29 (0.9H, s), 4.44 (0.9H, d, J=8.7 Hz), 4.31 (0.1H, d, J=8.5 Hz), 3.72 (1H, br d), 2.90 (1H, m), 1.49 (3H, m), 1.04 (9H, s) and 0.81 (6H,m). $^{13}$C-NMR; δ ((CD$_3$)$_2$SO, 9:1 mixture of diastereomers), 173.5, 172.9, 170.7, 170.6, 168.7, 150.1, 150.0, 145.3, 145.3, 113.5, 113.2, 71.2, 61.0, 60.8, 47.5, 46.6, 37.2, 36.1, 34.3, 34.1, 26.6, 26.4, 25.2, 23.8, 23.4, 21.7 and 21.4.

EXAMPLE 11

3R-(2,2-Dimethyl-1S-pyrid-3-ylcarbamoyl-propylcarbamoyl)-2S-hydroxy-5-methylhexanohydroxamic acid

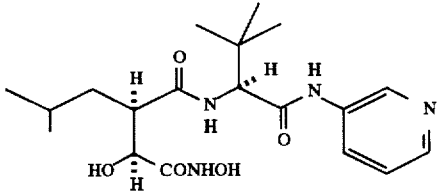

White solid. m.p 108°–112° C. $^1$H-NMR; δ ((CD$_3$)$_2$SO), 10.60 (1H, s), 10.26 (1H, s), 8.90 (1H, s), 8.74 (1H, s), 8.26 (1H, d, J=4.4 Hz), 8.05 (1H, d, J=8.2 Hz), 7.77 (1H, d, J=8.7 Hz), 7.36 (1H, m), 5.32 (1H, d, J=8.2 Hz), 4.45 (1H, d, J=8.9 Hz), 3.75 (1H, m), 2.81 (1H, m), 1.40 (3H, m), 0.98 (9H, s) and 0.80 (6H, dd, J=12.5, 6.2 Hz). $^{13}$C-NMR; δ (CD$_3$)$_2$SO, 172.7, 169.8, 168.7, 144.2, 140.9, 135.3, 126.2, 123.5, 71.2, 60.5, 47.6, 37.3, 34.3, 26.5, 25.3, 23.4 and 21.7. Found: C 54.46, H 7.46, N 13.42%; C$_{19}$H$_{30}$N$_4$O$_5$.1.2 H$_2$O requires C 54.85, H 7.85, N 13.46%.

EXAMPLE 12

3R-(2,2-Dimethyl-1S-(4-hydroxyphenyl)carbamoyl-propylcarbamoyl)-2S-hydroxy-5-methylhexanohydroxamic acid

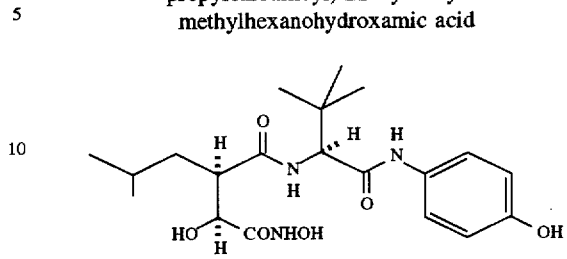

White solid. m.p. 138°–147° C. $^1$H-NMR; δ ((CD$_3$)$_2$SO), 10.59 (1H, s), 9.71 (1H, s), 9.17 (1H, s), 8.88 (1H, s), 7.61 (1H, d, J=9.2 Hz), 7.36 (2H, d, J=8.7 Hz), 6.69 (2H, d, J=8.7 Hz), 5.29 (1H, d, J=8.7 Hz), 4.40 (1H, d, J=9.2 Hz), 2.80 (1H, m), 1.49 (2H, m), 1.29 (1H, m), 0.95 (9H, s) and 0.80 (3H, d, J=6.4 Hz) and 0.75 (3H, d, J=6.4 Hz). $^{13}$C-NMR; δ ((CD$_3$)$_2$SO), 172.4, 168.7, 168.4, 153.3, 130.3, 121.1, 114.9, 71.3, 60.3, 47.7, 37.2, 34.7, 26.6, 25.3, 23.4 and 21.7. Found: C 57.28%, H 7.67%, N 10.17%; C$_{20}$H$_{31}$N$_3$O$_6$.0.5 H$_2$O requires C 57.40%, H 7.71%, N 10.04%.

EXAMPLE 13

3R-(2,2-Dimethyl-1S-(3-methoxyphenyl)carbamoyl-propylcarbamoyl)-2S-hydroxy-5-methylhexanohydroxamic acid

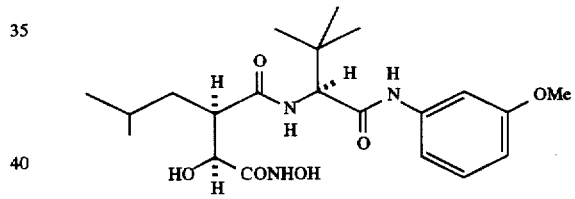

White solid. m.p. 97°–102° C. $^1$H-NMR; δ ((CD$_3$)$_2$SO), 10.58 (1H, s), 9.96 (1H, s), 8.87 (1H, s), 7.67 (1H, d, J=9.2 Hz), 7.29 (1H, s), 7.20 (2H, m), 6.64 (1H, d, J=7.8 Hz), 5.29 (1H, d, J=7.9 Hz), 4.43 (1H, d, J=9 Hz), 3.72 (3H, s), 2.77 (1H, m), 1.50 (3H, m), 0.97 (9H, s), 0.81 (3H, d, J=6.4 Hz) and 0.78 (3H, d, J=6.4 Hz). $^{13}$C-NMR; δ ((CD$_3$)$_2$SO), 172.6, 169.3, 168.7, 159.4, 139.8, 129.4, 111.6, 108.6, 105.2, 71.3, 60.5, 54.9, 47.6, 37.3, 34.4, 26.5, 25.3, 23.4 and 21.8. Found: C 57.96%, H 7.58% N 9.39%; C$_{21}$H$_{33}$N$_3$O$_6$.0.7 H$_2$O requires C 57.84%, H 7.95%, N 9.63%.

EXAMPLE 14

3R-(2-Benzylthio-2-methyl-1S-(pyridin-2-ylcarbamoyl)propylcarbamoyl)-2S-hydroxy-5-methylhexanohydroxamic acid

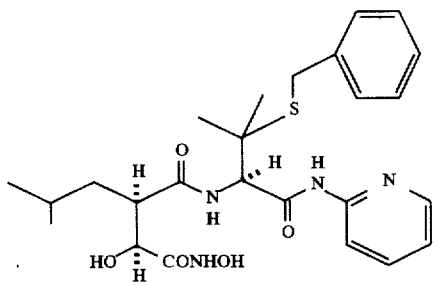

White foam. m.p. 112°–115° C. $^1$H-NMR; δ (CD$_3$OD), 8.26 (1H, m), 8.06 (1H, d, J=8.4 Hz), 7.73 (1H, m), 7.11–7.29 (5H, m), 7.07 (1H, m), 4.68 (1H, s), 4.15 (1H, d, J=4.7 Hz), 3.80 (2H, m), 2.93 (1H, m), 1.55–1.71 (1H, m), 1.48.(3H, s), 1.44 (3H, s), 1.47–1.23 (2H, br m), 0.90 (3H, d, J=6.4 Hz) and 0.84 (3H, d, J=6.3 Hz). $^{13}$C-NMR; δ (CD$_3$OD), 175.7, 171.7, 170.5, 152.3, 149.0, 139.8, 138.8, 130.3, 129.4, 128.0, 121.4, 115.9, 73.0, 61.4, 49.5, 49.3, 39.8, 34.2, 32.8, 26.9, 26.9, 26.2, 23.6 and 22.4. Found: C 59.78%, H 6.97%, N 10.86%; C$_{25}$H$_{34}$N$_4$O$_5$S requires C 59.74%, H 6.82% N 11.15%

EXAMPLE 15

3R-(2,2-Dimethyl-1S-(thiazol-2-ylcarbamoyl)-propylcarbamoyl)-2S-hydroxy-5-methylhexanohydroxamic acid

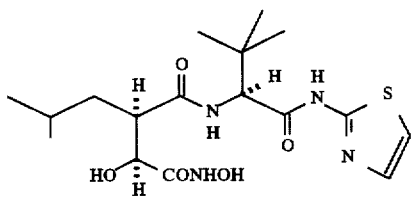

White solid. m.p. 125°–128° C. $^1$H-NMR; δ ((CD$_3$)$_2$SO), 10.60 (1H, s), 8.86 (1H, s), 7.80 (1H, d, J=8.4 Hz), 7.47 (1H, d, J=3.5 Hz), 7.22 (1H, d, J=3.5 Hz), 5.22 (J=1H, d, J=7.9 Hz), 4.52 (1H, d, J=8.3 Hz), 3.74 (1H, m), 2.83 (1H, m), 1.45 (3H, m), 0.96 (9H, s) 0.79 (3H, d, J=6.2 Hz) and 0.72 (3H, d, J=6.2 Hz). $^{13}$C-NMR; δ ((CD$_3$)$_2$SO), 172.9, 169.3, 168.7, 157.4, 137.6, 113.5, 71.3, 59.9, 47.4, 37.2, 34.1, 26.4, 25.2, 23.5 and 21.7.

EXAMPLE 16

3R-(2,2-Dimethyl-1S-phenylcarbamoyl-propylcarbamoyl)-2S-hydroxy-5-phenylhexanohydroxamic acid

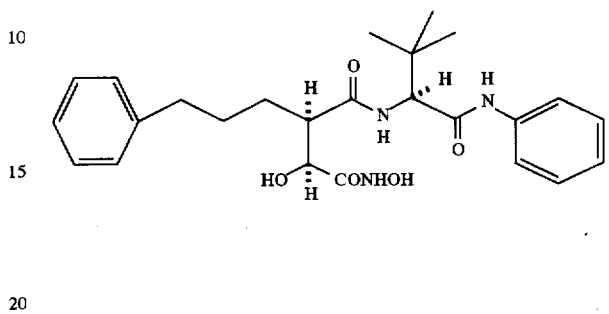

Mixture of diastereoisomers (4:1, SRS:RRS).

White solid. m.p. 98° C. $^1$H-NMR; δ (CD$_3$OD) 7.55–7.47 (2H, m), 7.28–7.21 (2H, m), 7.12–7.01 (6H, m), 4.47–4.44 (0.8H, m), 4.39–4.35 (0.2H, m), 4.26 (0.2H, d, J=4.8 Hz), 4.06 (0.8H, d, J=6.5 Hz), 2.87–2.83 (1H, m), 2.57–2.48 (2H, m), 1.81–1.52 (4H, m), and 1.03 (9H, s). $^{13}$C-NMR; δ (CD$_3$OD), 175.7, 171.5, 171.3, 143.3, 139.2, 129.6, 129.4, 129.3, 126.7, 125.5, 121.8, 73.0, 70.1, 62.6, 51.0, 36.7, 35.6, 30.3, 27.3 and 23.1. Found: C 65.05, H 7.57, N 8.78%; C$_{25}$H$_{33}$N$_3$O$_5$.0.3 H$_2$O requires C 65.06%, H 7.57%, N 8.78%.

EXAMPLE 17

3R-(2,2-Dimethyl-1S-(4,5-dimethylthiazol-2-ylcarbamoyl)-propylcarbamoyl)-2S-hydroxy-5-methylhexanohydroxamic acid

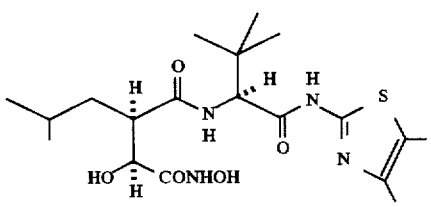

White solid. m.p. 191.5–192∞C. $^1$H-NMR; δ ((CD$_3$)$_2$SO), 11.84 (1H, s), 10.62 (1H, s), 8.87 (1H, s), 7.73 (1H, d, J=8.5 Hz), 5.23 (1H, d, J=7.9 Hz), 4.48 (1H, d, J=8.5 Hz), 3.70 (1H, m), 2.79 (1H, m), 2.49 (3H, s), 2.22 (3H, s), 1.41 (2H, m), 0.94 (10H, s and br m), 0.72 (3H, d, J=6.2 Hz) and 0.78 (3H, d, J=6.2 Hz). $^{13}$C-NMR; δ ((CD$_3$)$_2$SO), 171.5, 167.6, 167.4, 151.7, 140.4, 117.4, 70.1, 58.6, 46.2, 35.9, 32.9, 25.1, 24.0, 22.2, 20.5, 12.9 and 8.9. IR (KBr disk), ν$_{max}$ 1654 and 1535 cm$^{-1}$.

EXAMPLE 18

3R-(2,2-Dimethyl-1S-(4-ethoxycarbonylmethylthiazol-2-ylcarbamoyl)-propyl-carbamoyl)-2S-hydroxy-5-methylhexanohydroxamic acid

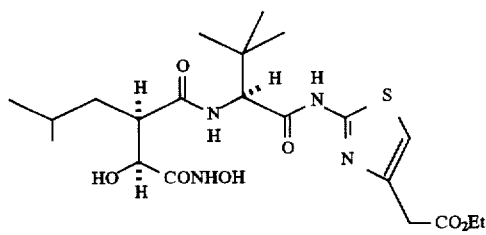

White solid. m.p. 104.5–11 0.5∞C. $^1$H-NMR; δ ((CD$_3$)$_2$SO), 12.17 (1H, s), 10.61 (1H, s), 8.87 (1H, s), 7.75 (1H, d, J=7.9 Hz), 6.97 (1H, s), 5.23 (1H, d, J=7.9 Hz), 4.48 (1H, d, J=8.3 Hz), 4.06 (2H, q, J=7.2 Hz), 3.67 (3H, m), 2.85 (1H, m), 1.40 (2H, m), 1.18 (3H, t, J=7.0 Hz), 0.96(10H, s and br m), 0.78(3H, d, J=6.3 Hz) and 0.72 (3H, d, J=6.3 Hz). $^{13}$C-NMR; δ ((CD$_3$)$_2$SO), 182.4, 178.9, 178.2, 166.6, 153.2, 119.9, 80.9, 69.8, 69.6, 56.9, 46.1, 45.9, 43.6, 35.9, 34.7, 33.0, 31.2 and 23.6. IR (KBr disc); $v_{max}$ 1735, 1644, 1549 cm$^{-1}$. Found: C 51.44, H 7.06, N 11.14%; C$_{21}$H$_{34}$N$_4$O$_7$S.0.2 H$_2$O requires C 51.46, H 7.07, N 11.43%.

EXAMPLE 19

3R-(2,2-Dimethyl-1S-(5-bromo-thiazol-2-ylcarbamoyl)-propylcarbamoyl)-2S-hydroxy-5-methylhexanohydroxamic acid

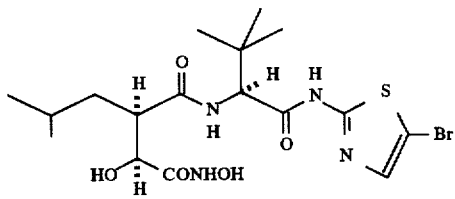

White solid. m.p. 196–198∞C. $^1$H-NMR; δ ((CD$_3$)$_2$SO), 8.74 (1H, s), 7.70 (1H, d, J=8.2 Hz), 7.41 (1H, s), 5.09 (1H, d, J=6.3 Hz), 4.36 (1H, d, J=8.2 Hz), 3.63–3.52 (1H, m), 2.73–2.60 (1H, m), 1.35–1.14 (2H, m), 0.93–0.72 (1H, m), 0.81 (9H, s), 0.65 (3H, d, J=6.3 Hz) and 0.58 (3H, d, J=6.3 Hz). $^{13}$C-NMR; δ ((CD$_3$)$_2$SO), 173.1, 170.0, 168.7, 157.7, 138.7, 101.7, 67.3, 59.9, 47.4, 37.2, 34.0, 26.4, 25.3, 23.5 and 21.8. IR (KBr disc); $v_{max}$ 3236, 2966, 1659 and 1534 cm$^{-1}$.

EXAMPLE 20

3R-(2,2-Dimethyl-1S-(4-phenyl-thiazol-2-ylcarbamoyl)-propylcarbamoyl)-2S-hydroxy-5-methylhexanohydroxamic acid

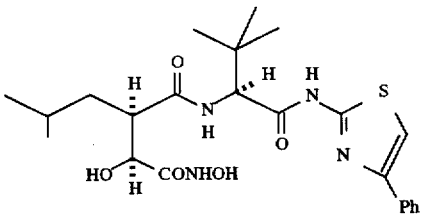

White solid. m.p. 158°–160° C. $^1$H-NMR; δ ((CD$_3$)$_2$SO), 8.74 (1H, s), 7.80–7.64 (3H, m), 7.45 (1H, s), 7.33–7.12 (3H, m), 4.42 (1H, d, J=8.3 Hz), 5.39 (1H, d, J=8.6 Hz), 2.77–2.63 (1H, m), 1.39–1.16 (2H, m), 0.84 (9H, s), 0.94–0.73 (1H, m), 0.67 (3H, d, J=6.4 Hz) and 0.59 (3H, d, J=6.4 Hz). $^{13}$C-NMR; δ ((CD$_3$)$_2$SO), 173.0, 169.8, 168.8, 157.4, 148.9, 134.3, 128.7, 127.7, 125.7, 108.1, 71.4, 60.1, 47.5, 37.2, 34.1, 26.5, 25.3, 23.5 and 21.8. IR (KBr disc); $v_{max}$ 3310, 2956, 1653, 1541 cm$^{-1}$. Found: C 55.69, H 6.82, N 11.15%; C$_{23}$H$_{32}$N$_4$O$_5$S.1.1H$_2$O requires C 55.65, H 6.94, N 11.29%.

EXAMPLE 21

3R-(2,2-Dimethyl-1S-(5-methylthiadiazol-2-ylcarbamoyl)-propylcarbamoyl)-2S-hydroxy-5-methylhexanohydroxamic acid

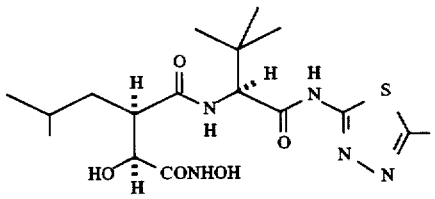

White solid. m.p. 159°–161° C. $^1$H-NMR; δ ((CD$_3$)$_2$SO), 8.73 (1H, m), 7.69 (1H, d, J=8.2 Hz), 5.10 (1H, m), 4.38 (1H, d, J=8.0 Hz), 3.58 (1H, m), 2.69 (1H, m), 2.45 (3H, s), 1.36–1.12 (2H, m), 0.94–0.73 1H, m), 0.82 (9H, s), 0.65 (3H, d, J=6.3 Hz) and 0.58 (3H, d, J=6.3 Hz). $^{13}$C-NMR; δ ((CD$_3$)$_2$SO), 173.1, 169.6, 159.4, 157.9, 71.3, 60.2, 47.4, 37.2, 34.0, 28.4, 25.3, 23.5, 21.8 and 14.7. IR (KBr disc); $v_{max}$ 3260, 2959, 1655, 1540 and 1311 cm$^{-1}$. Found: C 46.71, H 7.24 N 16.02%; C$_{17}$H$_{29}$N$_5$O$_5$S.1.2H$_2$O requires C 46.71, H 7.24, N 16.02%.

EXAMPLE 22

3R-(2,2-Dimethyl-1S-(4-tert-butylthiadiazol-2-ylcarbamoyl)-propylcarbamoyl)-2S-hydroxy-5-methylhexanohydroxamic acid

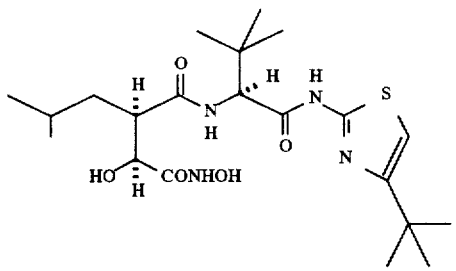

White solid. m.p. 169–171∞C. $^1$H-NMR; d (($CD_3$)$_2$SO), 8.73 (1H, s), 7.60 (1H, d, J=8.3 Hz), 6.58 (1H, s), 5.09 (1H, d, J=7.9 Hz), 4.34 (1H, d, J=8.3 Hz), 3.56 (1H, dd, J=8.3 Hz), 3.74–2.60 (1H, m), 1.39–1.03 (2H, m), 1.11 (9H, s), 0.92–0.70 (1H, m), 0.82 (9H, s), 0.65 (3H, d, J=6.3 Hz) and 0.58 (3H, d, J=6.3 Hz). $^{13}$C-NMR; d (($CD_3$)$_2$SO), 172.9, 169.4, 168.7, 160.2, 156.7, 104.7, 71.4, 60.1, 47.4, 37.2, 34.1, 34.0, 29.8, 26.5, 25.2, 23.6 and 21.7. IR (KBr disc); $n_{max}$ 3270, 2962, 1668, 1557, 1368, 1270 cm$^{-1}$. Found: C 53.74, H 8.18, N 11.45%; $C_{21}H_{36}N_4O_5S$.0.9 $H_2O$ requires C 53.35, H 8.06, N 11.85%.

EXAMPLE 23

R-(2,2-Dimethyl-1S-pyridin-2-ylcarbamoyl-propylcarbamoyl)-5-methyl-2S-propen-2-yl-hexanohydroxamic acid

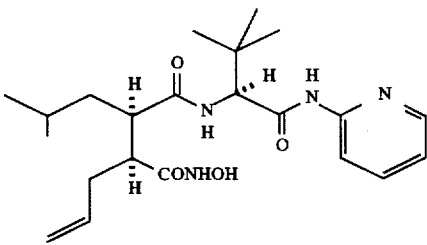

STEP A

3R,S-Allyl-2R-isobutyl-butan-1,4-dioic acid-4-tert-butyl ester (1:9, RS:RR)

To a stirred solution of 2R-isobutyl-1,4-dioic acid-4-tert-butyl ester (5 g, 21.7 mmol) in dry THF (100 ml), under an argon atmosphere, at −78° C., was added 1.5M LDA (31.8 ml, 47.7 mmol) dropwise via cannula. After stirring the solution at −78° C. for 1 hour, allyl bromide (2.44 ml, 28.2 mmol) was added dropwise via syringe. The resulting solution was allowed to warm to room temperature over a 2 hour period. Methanol (10 ml) was added and the solution stirred at room temperature. After 30 minutes the reaction mixture was concentrated under reduced pressure. The residue was taken up in dichloromethane (100 ml) and washed with 1M hydrochloric acid (100 ml) and brine (100 ml). The dichloromethane layer was dried over anhydrous magnesium sulphate filtered and solvent removed under reduced pressure to give the title compound as a golden oil (5.6 g, 97%) (1:9, RS:RR) $^1$H-NMR; δ (CDCl$_3$ major diastereoisomer), 5.78–5.63 (1H, m), 5.01–5.11 (2H, m), 2.57–2.72 (2H, m), 2.37 (2H, m), 1.52–1.67 (2H, m), 1.42 (9H, s), 1.37 (1H, m), and 0.90 (6H, d, J=6.3 Hz). $^{13}$C-NMR; δ (CDCl$_3$, major diastereoisomer) 181.1, 172.9, 134.6, 117.3, 81.2, 47.8, 44.3, 38.4, 27.9, 25.9, 23.5, and 21.5.

STEP B

3R,S-Allyl-2R-isobutyl-1,4-dioic acid-4-tert-butyl ester (3:1, RS:RR)

(i) To a stirred solution of 3R,S-allyl-2R-isobutyl-1,4-dioic acid-4-tert-butyl ester (1:9, RS:RR) (5.11 g, 18.9 mmol) in dry THF (100 ml) under argon at −78° C. was added 1.5M LDA (27.7 ml, 41.6 mmol) via cannula. The reaction mixture was warmed to room temperature over a 2 hour period then cooled back to −78° C. and methanol (8 ml) was added via syringe. The reaction was then allowed to warm to room temperature for a further 2 hours. The solvent was removed under reduced pressure. The residue was taken up in dichloromethane (150 ml) and washed with 1M hydrochloric acid (150 ml) and brine (150 ml). The dichloromethane layer was dried over anhydrous magnesium sulphate, filtered and the solvent removed under reduced pressure to yield the title compound (3:2, RS:RR), as a brown oil (4.7 g, 92%).

(ii) Utilising the epimerisation procedure described in Example 23B (i), but employing a reaction temperature of −78° C. after addition of LDA in lieu of allowing the reaction mixture to warm to room temperature yielded the title compound, as the major diastereoisomer as a brown oil (4.6 g, 98%) (3:1, RS:RR). $^1$H-NMR; δ (CDCl$_3$, major diastereoisomer), 11.60 (1H, br s), 5.75–5.61(1H, br m), 5.06–4.96 (2H, br m), 2.70–2.52 (2H, br m), 2.36–2.19 (2H, br m), 1.65–1.44 (2H, br m), 1.40 (9H, s), 1.13 (1H, m) and 0.86 (6H, dd, J=4.4, 2.1 Hz). $^{13}$C-NMR; δ (CDCl$_3$, major diastereoisomer) 180.7, 172.2, 134.6, 117.1, 81.0, 48.6, 45.7, 38.9, 34.8, 33.4, 27.9, 26.2 and 21.2.

STEP C

3R,S-Allyl-2R-isobutyl-1,4-dioic acid-1-pentafluorophenyl-4 tert-butyl diester (3:1, RS:RR)

To a stirred solution of 3R,S-allyl-2R-isobutyl-1,4-dioic acid-4 tert-butyl diester (4.60 g, 17.2 mmol) (3:1, RS:RR) in dichloromethane (50 ml) was added pentafluorophenol (6.13 g, 33.3 mmol). The reaction mixture was cooled to 0° C. and NMM (2.02 g, 20.0 mmol) and EDC (3.94 g, 20.0 mmol) were added. The reaction mixture was allowed to warm to room temperature and stirred for 12 hours. The solvent was removed under reduced pressure. The residue was taken up in dichloromethane (50 ml) and washed with 1M hydrochloric acid (3×50 ml), saturated sodium hydrogen carbonate (3×50 ml) and brine (50 ml). The dichloromethane layer was dried over anhydrous magnesium sulphate, filtered and the solvent removed under reduced pressure to give a brown oil. Column chromatography (silica gel, dichloromethane) yielded the title compound as a golden oil (5.47 g, 74%) (3:1, RS:SR). δ (CDCl$_3$, major diastereoisomer), 5.85–567 (1H, br m), 5.17–5.05 (2H, br m), 3.10–3.01 (1H, m), 2.79–2.69 (1H, m), 2.51–2.29 (2H, br m), 1.88–1.61 (2H, br m), 1.46 (9H, s), 1.37–1.24 (1H, m) and 0.96 (6H, dd, J=4.0, 4.5 Hz). $^{13}$C-NMR; δ (CDCl$_3$, major diastereoisomer), 171.5, 170.3, 134.1, 117.5, 81.4, 48.8, 45.8, 39.5, 35.0, 27.9, 26.3, 23.5, and 21.0.

STEP D

L-tert-leucine-2-pyridylamide

The title compound was prepared from $N^\alpha$-benzyloxycarbonyl-L-tert-leucine by methods analogous to those described in Example 1 (Steps D and E). ¹H-NMR; δ (CDCl₃), 8.26 (1H, m), 8.10 (1H, m), 7.74 (1H, m), 7.06 (1H, m), 3.25 (1H, s), 1.00 (9H, s).

STEP E

3R-(2,2-Dimethyl-1S-pyridin-2-ylcarbamoyl-propylcarbamoyl)-5-methyl-2S-propen-2-yl-hexanoic acid-1-tert-butyl ester The products from 3R,S-allyl-2R-isobutyl-1,4-doic acid-1-pentafluorophenyl-4-tert-butyl diester (3:1, RS:RR) (5.59 g, 12.8 mmol) and L-tert-leucine-2-pyridylamide (2.91 g, 14.1 mmol) were dissolved together in DMF (50 ml) and stirred at 30° C. for 40 hours. TLC revealed that all of the pentafluorophenyl ester had been consumed. The solvent was removed and the residue was purified by column chromatography (silica gel, ethyl acetate-hexane, 1:1) and crystallisation from ethyl acetate-hexane. Yield: 1.41 g (24%, 5:1 mixture of SRS:RRS diastereoisomers). ¹H-NMR; δ (CDCl₃, major diastereoisomer), 9.58 (1H, m), 8.52 (1H, m), 8.19 (1H, d, J=8.3 Hz), 7.73 (1H, m), 7.12 (1H, m), 6.49 (1H, d, J=9.2 Hz), 5.76 (1H, m), 5.05 (1H, m), 4.62 (1H, d, J=9.2 Hz), 2.68 (1H, m), 2.53 (1H, m), 2.29 (2H, m), 1.73 (1H, m), 1.47 (1H, m), 1.45 (9H, s), 1.15 (1H, m), 1.02 (9H, s), 0.87 (3H, d, J=6.5 Hz) and 0.79 (3H, d, J=6.5 Hz).

STEP F

3R-(2,2-Dimethyl-1S-pyridin-2-ylcarbamoyl-propylcarbamoyl)-5-methyl-2S-propen-2-yl-hexanoic acid 3R-(2,2-Dimethyl-1S-pyridin-2-ylcarbamoyl-propylcarbamoyl)-5-methyl-2S-propen-2-yl-hexanoic acid-1-tert-butyl ester (1.74 g, 3.78 mmol) was deprotected by TFA acidolysis according to the method described in Example 1 (Step G), affording the title compound contaminated with residual TFA. Yield: 1.61 g (contains solvent), 5:1 mixture of diastereoisomers. ¹H-NMR; δ (CD₃OD, major diastereoisomer), 8.29 (1H, m), 7.90 (2H, m), 7.23 (1H, m), 5.72 (1H, m), 4.99 (2H, m), 4.46 (1H, s), 2.80 (1H, dt, J=3.3, 10.8 Hz), 2.52 (1H, dt, 4.3, 10.2 Hz), 2.40–2.12 (2H, br m), 1.62 (1H, m), 1.42 (1H, m), 1.10 (2H, m), 1.08 (9H, s), 0.86 (3H, d, J=6.5 Hz) and 0.75 (3H, d, J=6.6 Hz).

STEP G

3R-(2,2-Dimethyl-1S-pyridin-2-ylcarbamoyl-propylcarbamoyl)-5-methyl-2S-propen-2-yl-hexanohydroxamic acid 3R-(2,2-Dimethyl-1S-pyridin-2-ylcarbamoyl-propylcarbamoyl)-5-methyl-2S-propen-2-yl-hexanoic acid (1.5 g, 3.71 mmol) was dissolved in DMF (5 ml) and the solution was cooled to 0° C. during the addition of HOBt (0.60 g, 4.46 mmol) and EDC (0.86 g, 4.46 mmol). The mixture was stirred at 0° C. for 1 hour then at room temperature for 2 hours to ensure complete formation of the active ester. The solution was cooled back to 0° C., hydroxylamine hydrochloride (0.39 g, 5.57 mmol) was added followed by NMM (0.56 g, 5.57 mmol) and the reaction mixture was allowed to warm to room temperature then stirred overnight. The solvent was removed in vacuo and the residue was triturated with a mixture of diethyl ether (25 ml) and water (25 ml) and left to stand for 2 hours. The resulting solid was collected by filtration, recrystallised from methanol-DIPE and dried under high vacuum at 60° C. for 24 hours to afford the title compound (0.62 g, 40%; single diastereoisomer) containing ca. 0.4 mol DIPE (NMR). m.p. 221–223∞C. ¹H-NMR; δ (CD₃OD), 8.26 (1H, m), 8.04 (1H, d, J=8.3 Hz), 7.72 (1H, dt, J=1.9, 5.5 Hz), 7.07 (1H, m), 5.64 (1H, m), 4.96 (2H, m), 4.52 (1H, s), 2.72 (1H, m), 2.26 (2H, m), 2.10 (1H, m), 1.50 (1H, m), 1.39 (1H, m), 1.06 (9H, s), 1.07 (1H, m), 0.84 (3H, d, J=6.4 Hz) and 0.73 (3H, d, J=6.5 Hz). ¹³C-NMR; δ (CD₃OD), 176.8, 172.4, 171.4, 152.7, 149.1, 139.4, 136.0, 121.1, 117.5, 115.7, 63.1, 48.2, 47.8, 41.8, 36.4, 35.3, 27.3, 27.0, 24.4 and 21.9. Found: C 63.68, H 8.66, N 12.08%; $C_{22}H_{34}N_4O_4$.0.4 $C_6H_{14}O$ requires: C 63.79, H 8.69, N 12.20%.

The following additional compounds were prepared according to the methods of Example 23:

EXAMPLE 24

3R-(2,2-Dimethyl-1S-phenylcarbamoyl-propylcarbamoyl)-5-methyl-2S-propen-2-yl-hexanohydroxamic acid

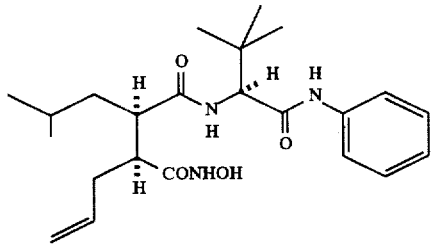

White solid. m.p. 211.5°–212.5° C. ¹H NMR; δ (CD₃OD), 7.45 (2H, m), 7.26 (2H, m), 7.05 (1H, m), 5.66 (1H, m), 4.96 (2H, m), 4.46 (1H, s), 2.73 (1H, m), 2.26 (2H, m), 2.11 (1H, m), 1.49 (1H, m), 1.48 (1H, m), 1.08 (1H, m), 1.06 (9H, s), 0.84 (3H, d, J=6.4 Hz) and 0.75 (3H, d, J=6.5 Hz). ¹³C-NMR; δ (CD₃OD), 176.7, 173.0, 171.0, 139.3, 136.1, 129.8, 125.8, 121.6, 117.5, 62.9, 48.2, 41.8, 36.4, 35.4, 27.3, 27.1, 24.4 and 21.9. Found: C 63.68, H 8.55 N 9.69%; $C_{23}H_{35}N_3O_4$.0.9$H_2O$ requires C 63.69, H 8.55, N 9.69%.

EXAMPLE 25

3R-(2,2-Dimethyl-1S-(thiazol-2-ylcarbamoyl)-propylcarbamoyl)-5-methyl-2S-propen-2-yl-hexanohydroxamic acid

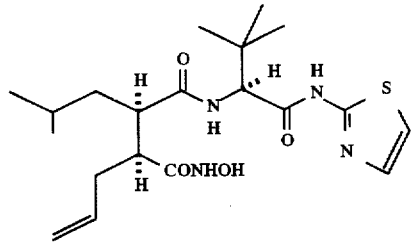

White solid. m.p.>300° C. ¹H-NMR; δ ((CD₃)₂SO), 12.10 (1H, s), 10.46 (1H, s), 8.77 (1H, s), 8.12 (1H, d, J=7.9 Hz), 7.45 (1H, d, J=3.5 Hz), 7.20 (1H, d, J=3.5 Hz), 5.62 (1H, m), 4.93 (2H, m), 4.51 (1H, d, J=4.5 Hz), 2.82 (1H, m), 2.30 (1H, m), 2.22 (2H, m), 1.41 (3H, m), 0.98 (9H, s), 0.88 (3H, d, J=6.3 Hz) and 0.78 (3H, d, J=6.3 Hz). ¹³C-NMR; δ ((CD₃)₂SO), 174.1, 169.3, 169.2, 157.4, 137.7, 135.8, 116.2, 113.5, 60.3, 45.9, 45.3, 40.2, 34.9, 33.5, 26.5, 25.2, 24.0 and 21.7. Found: C 56.30%, H 7.70% N 12.70%; $C_{20}H_{32}N_4O_4S$.0.2$H_2O$ requires C 56.10%, H 7.63% N 13.09%.

EXAMPLE 26

3R-(2,2-Dimethyl-1S-(4-methoxyphenylcarbamoyl)-propylcarbamoyl)-5-methyl-2S-propen-2-yl-hexanohydroxamic acid

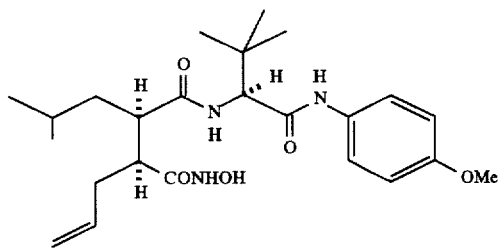

White crystalline solid. m.p. 213°–228° C. $^1$H-NMR; δ (CD$_3$OD), 8.13 (1H, d, J=9.0 Hz), 7.33 (2H, d, J=9.0 Hz), 6.81 (2H, d, J=9.0 Hz), 5.63 (1H, m), 4.97 (2H, m), 4.45 (1H, t, J=5.4, 3.6 Hz), 3.72 (3H, s), 2.73 (1H, m), 2.20 (3H, m), 1.43 (2H, m), 1.10 (1H, m), 1.06 (9H, s), 0.84 (3H, d, J=6.4 Hz), and 0.75 (3H, d, J=6.5 Hz). $^{13}$C-NMR; δ (CD$_3$OD), 176.7, 172.4, 170.8, 158.1, 136.0, 132.1, 123.5, 117.5, 115.0, 62.9, 55.9, 48.1, 41.9, 36.4, 35.4, 27.4, 27.1, 24.4 and 22.0. IR (KBr disc); ν$_{max}$ 3308, 2958, 1644, 1513, 1245, 1036 and 830 cm$^{-1}$. Found C 63.39, H 8.26, N 9.30%. C$_{24}$H$_{37}$N$_3$O$_5$·0.4H$_2$O requires C 63.39, H 8.38, N 9.24%.

EXAMPLE 27

3R-(2-Benzylthio-2-methyl-1S-(pyridin-2-ylcarbamoyl)-propylcarbamoyl)-5-methyl-2S-propen-2-yl-hexanohydroxamic acid

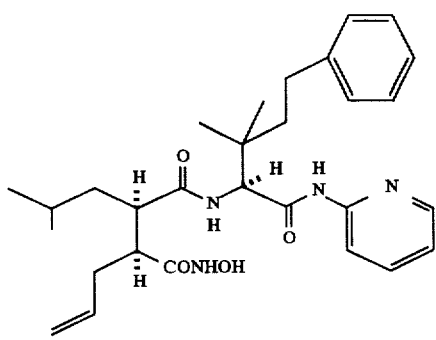

White solid. m.p. 214°–214.5° C. $^1$H-NMR; δ (CD$_3$OD at 338K), 8.36 (1H, m), 8.02 (1H, m), 7.72 (1H, m), 7.32–7.12 (5H, br m), 7.05 (1H, m), 5.62–5.53 (1H, br m), 4.96–4.82 (3H, br m), 3.87 (2H, m), 2.69 (1H, m), 2.37–2.21 (3H, m), 1.61–1.34 (2H, br m), 1.51 (3H, s), 1.45 (3H, s), 1.13 (1H, br m), 0.82 (3H, d, J=6.4 Hz) and 0.73 (3H, d, J=6.4 Hz). $^{13}$C-NMR; δ ((CD$_3$)$_2$SO), 172.8, 168.1, 167.9, 146.8, 136.9, 136.4, 134.9, 128.0, 127.0, 125.4, 118.4, 114.7, 112.5, 56.5, 47.2, 44.8, 44.4, 33.6, 31.2, 25.3, 24.2, 22.7, 22.64 and 20.4.

EXAMPLE 28

3R-(2,2-Dimethyl-1S-(pyridin-3-ylcarbamoyl)-propylcarbamoyl)-5-methyl-2S-propen-2-yl-hexanohydroxamic acid

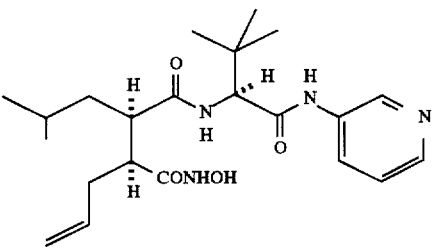

White solid. m.p. 220°–224° C. $^1$H-NMR; δ ((CD$_3$)$_2$SO), 10.30 (1H, s), 10.00 (1H, s), 8.73 (1H, s), 8.26 (1H, d, J=4.1 Hz), 7.99 (1H, d, J=8.2 Hz), 7.81 (1H, d, J=8.5 Hz), 7.34 (1H, m), 5.65 (1H, m), 4.93 (2H, m), 4.43 (1H, d, J=5.3 Hz), 2.74 (1H, m), 2.50–2.21 (3H, m), 1.50 (3H, m), 1.04 (9H, s), 0.83 (3H, d, J=6.4 Hz), and 0.77 (3H, d, J=6.3 Hz). $^{13}$C-NMR; δ ((CD$_3$)$_2$SO), 174.0, 169.7, 169.2, 144.2, 140.7, 135.8, 135.4, 126.0, 123.6, 116.1, 61.0, 45.9, 45.5, 34.9, 33.7, 26.6, 25.3, 24.0 and 21.7.

EXAMPLE 29

3R-(2,2-Dimethyl-1S-(4-hydroxyphenylcarbamoyl)-propylcarbamoyl)-5-methyl-2S-propen-2-yl-hexanohydroxamic acid

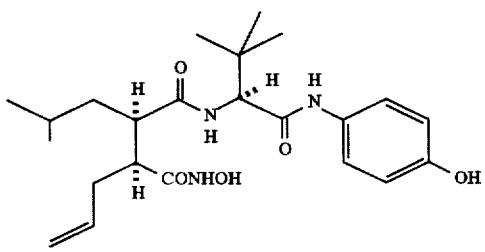

Yellow solid. $^1$H-NMR; δ ((CD$_3$)$_2$SO), 10.46 (1H, s), 9.70 (1H, s), 9.17 (1H, s), 8.77 (1H, s), 8.00 (1H, d, J=8.7 Hz), 7.31 (2H, d, J=8.8 Hz), 6.70 (2H, d, J=8.8 Hz), 5.67 (1H, m), 4.93 (2H, m), 4.38 (1H, d, J=8.7 Hz), 2.70 (1H, m), 2.31–2.19 (3H, m), 1.44 (3H, m), 0.98 (9H, s), 0.81 (3H, d, J=6.3 Hz) and 0.73 (3H, d, J=6.3 Hz). $^{13}$C-NMR; δ ((CD$_3$)$_2$SO), 173.8, 169.3, 168.4, 153.3, 135.9, 130.4, 121.0, 116.1, 114.9, 60.8, 45.8, 45.7, 34.9, 33.9, 26.7, 25.3, 24.0 and 21.7.

EXAMPLE 30

3R-(2,2-Dimethyl-1S-(3-methoxyphenylcarbamoyl)-propylcarbamoyl)-5-methyl-2S-propen-2-yl-hexanohydroxamic acid

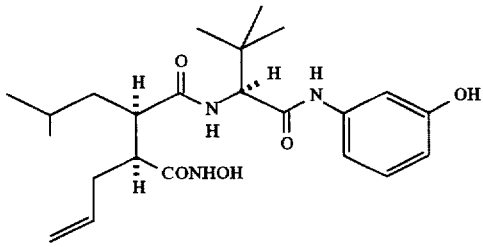

White solid. $^1$H-NMR; δ ((CD$_3$)$_2$SO), 10.45 (1H, s), 9.96 (1H, s), 8.77 (1H, s), 7.99 (1H, d, J=8.0 Hz), 7.40 (1H, s), 7.26 (2H, m), 6.60 (1H, d, J=7.8 Hz), 5.60 (1H, m), 4.93 (2H, m), 4.40 (1H, d, J=8.5 Hz), 3.72 (3H, s), 2.81 (1H, m), 2.10–2.49 (2H, m), 1.99 (1H, m), 1.44 (2H, m), 1.09 (9H, s), 0.99 (1H, m), 0.82 (3H, d, J=6.3 Hz) and 0.72 (3H, d). $^{13}$C-NMR; δ ((CD$_3$)$_2$SO), 173.9, 169.3, 159.5, 140.0, 135.9, 129.5, 116.2, 111.6, 108.5, 105.1, 61.1, 55.0, 45.9, 45.6, 40.3, 34.9, 33.9, 26.7, 25.3, 24.1 and 21.7.

EXAMPLE 31

3R-(2,2-Dimethyl-1S-(pyridin-4-ylcarbamoyl)-propylcarbamoyl)-5-methyl-2S-propen-2-yl-hexanohydroxamic acid

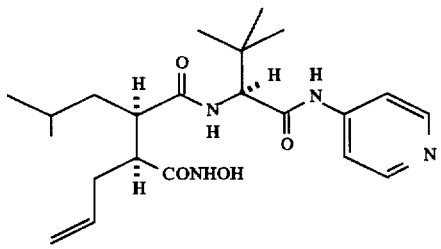

Pale pink solid. m.p. 210° C. (dec.). $^1$H-NMR; δ ((CD$_3$)$_2$SO), 10.15 (2H, s), 8.28 (2H, d, J=3.9 Hz), 7.73 (1H, d, J=8.1 Hz), 7.44 (2H, d, J=5.1 Hz), 5.51 (1H, m), 4.81 (2H, m), 4.26 (1H, d, J=8.4 Hz), 2.75 (1H, m), 2.36 (2H, m), 2.11 (1H, m), 1.24 (2H, m), 0.88 (9H, s), 0.84 (1H, m), 0.68 (3H, d, J=6.4 Hz) and 0.59 (3H, d, J=6.4 Hz). $^{13}$C-NMR; δ ((CD$_3$)$_2$SO), 172.8, 169.3, 167.9, 148.6, 144.3, 134.5, 114.8, 111.9, 60.1, 44.6, 44.1, 33.6, 32.3, 25.2, 23.9, 22.7 and 20.3.

EXAMPLE 32

3R-(2,2-Dimethyl-1S-(2-methoxyphenylcarbamoyl)-propylcarbamoyl)-5-methyl-2S-thien-2-ylsulfanylmethyl-hexanohydroxamic acid

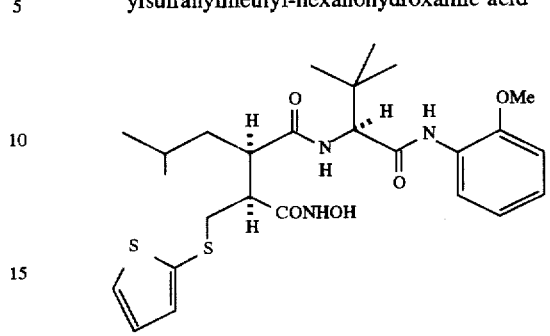

STEP A

2-Benzyloxycarbonyl-3R-(2,2-dimethyl-1S-(2-methoxyphenylcarbamoyl)-propylcarbamoyl)-5-methyl-hexanohydroxamic acid benzyl ester 2-Benzyloxycarbonyl-3R-carboxy-5-methylhexanoic acid benzyl ester (prepared by the method described in EP 0 446 267) (20.1 g, 50.5 mmol) and L-tert-leucine-N$^1$-(2-methoxyphenyl)amide (prepared according to the method described in Example 1, Steps D and E) (14.3 g, 60.6 mmol) were dissolved together in ethyl acetate (300 ml). HOBt (8.2 g, 60.6 mmol) and EDC (11.6 g, 60.6 mmol) were added and the mixture was stirred and heated at reflux overnight, after which TLC analysis showed that the reaction was complete. The solution was cooled and washed successively with 5% aq. sodium hydrogen carbonate (2×200 ml), 5% citric acid (2×200 ml) and brine (1×200 ml), dried over anhydrous magnesium sulphate, filtered and evaporated to give a brown oil (32.75 g, contained residual solvent) which was used in Step B without further purification. $^1$H-NMR; δ (CDCl$_3$), 8.07 (1H, s), 7.40–7.22 (10H, br m), 7.15 (1H, m), 6.96 (1H, m), 6.75 (1H, m), 6.65 (1H, m), 5.12–5.04 (3H, br m), 4.37 (1H, d, J=9.0 Hz), 3.85 (1H, d, J=9.6 Hz), 3.76 (3H, s), 3.08 (1H, m), 1.80–1.37 (3H, br m), 1.06 (9H, s), 0.79 (3H, d, J=6.4 Hz), 0.71 (3H, d, J=6.5 Hz).

STEP B

3R-(2,2-Dimethyl-1S-(2-methoxyphenylcarbamoyl)-propylcarbamoyl)-2-methylene-5-methyl-hexanohydroxamic acid 2-Benzyloxycarbonyl-3R-(2,2-dimethyl-1S-(2-methoxyphenylcarbamoyl)-propylcarbamoyl)-5-methyl-hexanohydroxamic acid benzyl ester (28.7 g, 45.40 mmol) was dissolved in ethanol (200 ml) and the solution was placed under a blanket of argon. 10% Palladium on charcoal was added and a fine stream of hydrogen gas was passed through the suspension for 3 h with stirring. TLC showed that all the starting material had been consumed. The system was purged with argon and the catalyst was removed by filtration. The filtrate was cooled and stirred in an ice bath and treated with piperidine (4.04 g, 47.4 mmol) which was added dropwise, followed by 37% formaldehyde solution (32.3 ml, ca. 430 mmol). The reaction mixture was allowed to warm slowly to room temperature, then stirred overnight. The solvents were removed under reduced pressure and the residual oil was partitioned between ethyl acetate (300 ml) and 1M hydrochloric acid (300 ml). The organic layer was separated, washed with 1M hydrochloric acid and brine, dried over magnesium sulphate and evaporated to dryness. The remaining pale brown foam (18.94 g, crude) contained a number of minor impurities but was used in Step C without purification. ¹H-NMR; δ (CD₃OD), 7.55 (1H, m), 7.09 (3H, m), 6.95 (1H, m), 6.59 (1H, m), 6.26 (1H, s), 5.72 (1H, s), 4.30 (1H, d, J=9.2 Hz), 3.67 (1H, s), 3.65 (1H, m), 1.70 (1H, m), 1.41 (2H, m), 0.91 (9H, s), 0.81 (3H, d, J=6.3 Hz), 0.76 (3H, d, J=6.3 Hz).

STEP C 3R-(2,2-Dimethyl-1S-(2-methoxyphenylcarbamoyl)-propylcarbamoyl)-5-methyl-2S-thien-2-ylsulfanylmethyl-hexanoic acid 3R-(2,2-Dimethyl-1S-(²-methoxyphenylcarbamoyl)-propylcarbamoyl)-2-methylene-5-methyl-hexanohydroxamic acid (20.43 g, 48.7 mmol) was dissolved in methanol and placed under a blanket of argon prior to addition of 2-mercaptothiophene (20 ml). The mixture was stirred overnight at 60∞ C. under argon with the exclusion of light. The solvent was removed under reduced pressure to leave an oil to which was added cold diethyl ether (200 ml). The product precipitated on standing in an ice bath and was removed by filtration and washing with thoroughly with cold diethyl ether. The product was further purified by trituration with hot ethyl acetate and column chromatography (silica gel, gradient elution, 0Æ20% methanol in dichloromethane). Fractions were combined and evaporated to yield the title compound as an off-white foam (18.80 g, 72%). ¹H-NMR; δ (CDCl₃), 7.33 (1H, m), 7.14–7.09 (2H, m), 7.10 (1H, m), 6.95–6.85 (2H, br m), 6.58 (1H, m), 4.31 (1H, s), 3.66 (3H, s), 2.99–2.58 (4H, br m), 1.60–1.48 (1H, m), 1.37–1.18 (1H, m), 1.01 (1H, m), 0.95 (9H, s), 0.75 (3H, d, J=6.5 Hz), 0.68 (3H, d, J=6.5 Hz).

STEP D 3R-(2,2-Dimethyl-1S-(2-methoxyphenylcarbamoyl)-propylcarbamoyl)-5-methyl-2S-thien-2-ylsulfanylmethyl-hexanohydroxamic acid To a ice-cooled solution of 3R-(2,2-dimethyl-1S-(2-methoxyphenylcarbamoyl)-propylcarbamoyl)-5-methyl-2S-thien-2-ylsulfanylmethyl-hexanoic acid (20.43 g, 38.1 mmol) in DMF (100 ml) was added HOBt (6.18 g, 45.7 mmol) followed by EDC (8.77 g, 45.7 mmol). The mixture was stirred at 0∞C. for 1 h then at room temperature for a further 2 h, cooled back to 0∞C. and treated with hydroxylamine hydrochloride (3.97 g, 57.2 mmol) and NMM (5.78 g, 57.2 mmol). The reaction mixture was stirred overnight at room temperature then evaporated to an oil which was triturated with 1:1 diethyl ether /water (240 ml) and left to stand for 1.5 h. The resulting precipitate was collected by filtration and washed thoroughly with cold diethyl ether. HOBt was removed by crystallisation from ethyl acetate and the mother liquors were evaporated to give the title compound as an orange foam (4.96 g, 24%). m.p. 191°–195° C. ¹H-NMR; δ (CD₃OD), 8.07 (1H, d, J=8.8 Hz), 7.31 (1H, m), 7.11 (2H, m), 7.02 (1H, m), 6.92 (1H, m), 6.86 (1H, m), 6.56 (1H, m), 4.28 (1H, m), 3.66 (3H, s), 3.00 (1H, m), 2.75 (1H, m), 2.62 (1H, m), 2.35 (1H, m), 1.43 (1H, m), 1.26 (1H, m), 1.03 (1H, m), 0.94 (9H, s), 0.75 (3H, d, J=6.4 Hz) and 0.67 (3H, d, J=6.6 Hz). ¹³C-NMR; δ ((CD₃)₂SO), 176.2, 171.2, 165.4, 161.9, 140.8, 135.2, 131.0, 130.9, 128.0, 114.0, 111.3, 107.7, 63.4, 56.0, 46.2, 42.0, 40.8, 35.8, 27.7, 27.4, 24.7 and 22.2. IR (KBr disk) ν$_{max}$ 3294, 3087, 2959, 1771, 1644, 1547, 1493, 1466, 1430, 1386 and 1369 cm–1. Found: C 57.80, H 6.99, N 7.74%; C₂₆H₃₇N₂O₅S₂.0.3H₂O requires C 57.71, H 7.00, N 7.77%.

The following additional compound was prepared according to the methods of Example 32:

EXAMPLE 33

3R-(2,2-Dimethyl-1S-(pyridin-2-ylcarbamoyl)-propylcarbamoyl)-5-methyl-2S-thien-2-ylsulfanylmethyl-hexanohydroxamic acid

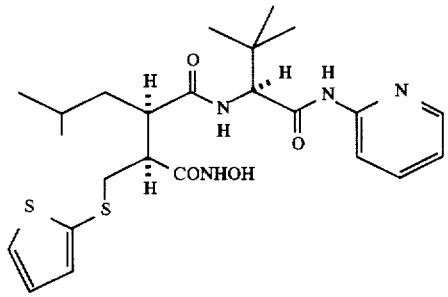

White crystalline solid. m.p. 199°–200° C. ¹H-NMR; δ ((CD₃)₂SO), 8.82 (1H, s), 8.15 (1H, m), 7.89 (1H, m), 7.86 (1H, m), 7.60 (1H, m), 7.44 (1H, m), 6.93 (2H, m), 6.87 (1H, m), 4.36 (1H, d, J=8.3 Hz), 3.04 (1H, m), 2.75 (1H, m), 2.56 (1H, m), 2.22 (1H, m), 1.29 (1H, m), 1.12 (1H, m), 0.90 (1H, m), 0.82 (9H, s), 0.65 (3H, d, J= 6.4 Hz) and 0.55 (3H, d, J=6.5 Hz). ¹³C-NMR; δ ((CD₃)₂SO), 173.1, 170.0, 167.9, 151.5, 148.0, 138.0, 133.8, 132.6, 129.6, 127.8, 119.3, 113.6; 60.7, 48.6, 46.0, 45.6, 33.6, 26.6, 25.2, 23.9 and 21.5. IR (KBr disc); ν$_{max}$ 3256, 2890, 2871 1651, 1579, 1520, 1466, 1435, 1369, 1298, 1217, 1152, 1054 and 1002 cm⁻¹.

EXAMPLE 34

3R-(2,2-Dimethyl-1S-(2-methoxyphenylcarbamoyl)-propylcarbamoyl)-5-methyl-2S-thien-2-ylsulfinylmethyl-hexanohydroxamic acid

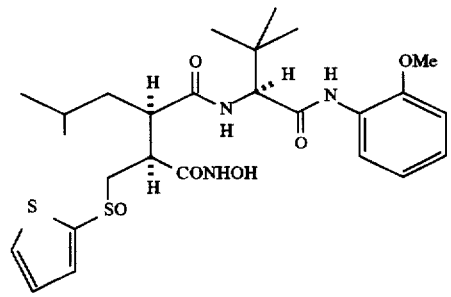

3R-(2,2-Dimethyl-1S-(2-methoxyphenylcarbamoyl)-propylcarbamoyl)-5-methyl-2S-thien-2-ylsulfanylmethyl-hexanohydroxamic acid (prepared in Example 32) (1.00 g, 1.81 mmol) was dissolved in methanol (20 ml) and cooled to 0∞C. in an ice bath during addition of mCPBA (0.34 g, 2.00 mmol). The reaction mixture was allowed to warm to room temperature, stirred for 4 h, and the solvent was removed under reduced pressure. The residue was triturated with diethyl ether leaving the crude product as a solid which was collected by filtration. Recrystallisation from ethyl acetate afforded the title compound as a white powder in two crops (304 mg, 30%). m.p. 210°–211° C. ¹H-NMR; δ (CD₃OD), 7.31 (1H, m), 7.01 (2H, m), 7.00 (1H, m), 6.81 (1H, m), 6.80 (1H, m), 6.56 (1H, m), 4.29 (1H, s), 3.65 (3H, s), 2.95 (1H, m), 2.73 (1H, m), 2.63 (1H, m), 2.37 (1H, m), 1.43 (1H, m), 1.26 (1H, m), 1.05 (1H, m), 0.95 (9H, s), 0.75 (3H, d, J=6.4 Hz) and 0.68 (3H, d, J=6.5 Hz). $^{13}$C-NMR; δ (CD$_3$OD), 175.5, 170.7, 170.6, 161.1, 140.0, 134.5, 130.3, 130.2, 128.2, 113.3, 110.6, 107.0, 62.6, 55.3, 41.3, 40.1, 35.1, 27.0, 26.7, 24.0 and 21.5. IR (KBr disc) $v_{max}$ 3292, 1614, 1538, 1489, 1428, 1371,1232, 1170 and 1047 cm$^{-1}$. Found: C 55.70, H 6.68, N 7.39%; C$_{26}$H$_{37}$N$_3$O$_6$S$_2$.0.5H$_2$O requires C 55.69, H 6.83, N 7.49%.

The following additional compound was prepared according to the methods of Example 34:

EXAMPLE 35

3R-(2,2-Dimethyl-1S-(pyridin-2-ylcarbamoyl)-propylcarbamoyl)-5-methyl-2S-thien-2-ylsulfinylmethyl-hexanohydroxamic acid

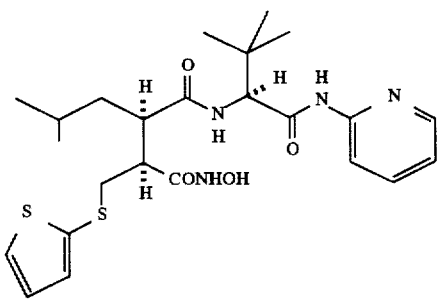

White powder. m.p. 166–166.5∞C. $^1$H-NMR; δ ((CD$_3$OD), 8.18 (1H, m), 7.94 (1H, m), 7.82 (1H, m), 7.64 (1H, m), 7.50 (1H, m), 7.10 (1H, m), 7.00 (1H, m), 4.42 (1H, m), 3.53 (1H, m), 2.99 (1H, m), 2.77 (1H, m), 2.19 (1H, m), 1.53 (1H, m), 1.34 (1H, m), 1.13 (1H, m), 0.98 (9H, s), 0.77 (3H, m), and 0.66 (3H, m). $^{13}$C-NMR; δ ((CD$_3$OD), 175.4, 171.2, 169.9, 152.7, 149.2, 144.8, 139.4, 134.2, 133.5, 128.6, 121.1, 115.6, 63.2, 61.2, 59.8, 43.2, 41.2, 35.3, 27.4, 27.0, 24.3 and 21.8. IR (KBr disc); $v_{max}$ 3259, 2959, 1647, 1578, 1529, 1467, 1435, 1369, 1297, 1224, 1152 and 1034 cm$^{-1}$ Found: C 53.64, H 6.52 N 10.33%; C$_{24}$H$_{34}$N$_4$O$_5$S$_2$.0.8 H$_2$O requires C 53.67, H 6.68, N 10.43%.

EXAMPLE 36

3R-(2,2-Dimethyl-1S-phenylcarbamoyl-propylcarbamoyl)-2S-hydroxy-5-phenylhexanoic acid

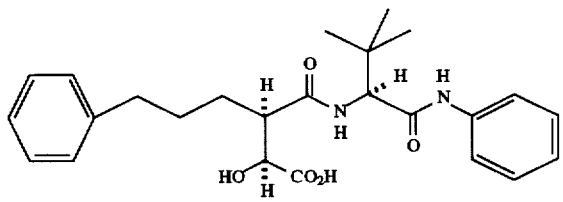

A solution of N$^2$-[2R-(2,2-dimethyl-4-oxo-1,3-dioxalan-5S-yl)-6-phenylhexanoyl]-L-tert-leucine-N$^1$-phenylamide (prepared by a method analogous to that described in Example 4) (1.00 g, 2.08 mmol) in THF (15 ml) was cooled to 0∞C. and 1M hydrochloric acid (15 ml) was added. The mixture was stirred at room temperature until TLC indicated that all of the starting material had been consumed (several days). The solvents were removed under reduced pressure to leave a pale yellow foam which was dissolved in ethyl acetate and filtered through a pad of silica. The product was purified further by extraction into 1M sodium carbonate solution, re-acidification with 1M hydrochloric acid and back extraction into ethyl acetate. The ethyl acetate layer was dried over magnesium sulphate, filtered and evaporated under reduced pressure to afford the title compound as an off-white foam (320 mg, 35%; 3:1 mixture of diastereoisomers). m.p. 159° C. $^1$H-NMR; δ (CD$_3$OD), 7.51–7.48 (2H, m), 7.26–7.00 (8H, m), 4.39 (1H, s), 4.25 (0.25H, d, J=3.7 Hz), 4.18 (0.75H, d, J=2.7 Hz), 2.90 (1H, br s), 2.56–2.51 (2H, br m), 1.74–1.56 (4H, m), and 1.02 (9H, s). $^{13}$C-NMR; δ (CD$_3$OD), 179.3, 176.9, 171.1, 143.4, 139.2, 129.7, 129.4, 129.3, 126.7, 125.5, 121.8, 73.6, 63.1, 50.9, 36.6, 35.6, 30.5 and 27.4. Found: C 66.07, H 7.21, N 5.98%; C$_{25}$H$_{32}$N$_2$O$_5$.0.8H$_2$O requires C 66.00, H 7.44, N 6.16%.

EXAMPLE 37

3R-(2,2-Dimethyl-1S-pyridin-2-ylcarbammoyl-propylcarbamoyl)-5-methyl-2S-phthalimidomethylhexanohydroxamic acid

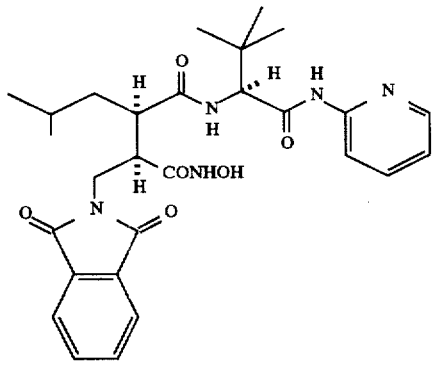

STEP A

2-Benzyloxycarbonyl-3R-tert-butoxycarbonyl-5-methyl-2-phthalimidomethylhexanoic acid benzyl ester To an ice-cooled solution of 2-benzyloxycarbonyl-3R-tert-butoxycarbonyl-5-methylhexanoic acid benzyl ester (prepared by the method described in EP 0 446 267) (39.4 g, 86.78 mmol) in dry DMF (400 ml) was added sodium hydride (60% dispersion in mineral oil, 3.83 g, 95.46 mmol) with stirring. The reaction mixture was maintained at 0∞C. for 20 mins then allowed to warm to room temperature and stirred for a further 2.5 h. After cooling to 0∞C., N-bromomethyl)phthalimide (25 g, 104.1 mmol) was added and the mixture was stirred for 0.5 h at 0∞C. then at room temperature overnight. The solvent was removed under reduced pressure to leave an oil which was extracted with diethyl ether (400 ml) and the solid residues were removed by filtration. The filtrate was washed successively with water (300 ml), 1M hydrochloric acid (300 ml) and brine (300 ml), dried over anhydrous magnesium sulphate and filtered. The solution was concentrated in vacuo to leave a yellow oil which was purified by column chromatography (silica gel, 50% diethyl ether in hexane) to afford the title compound as a colourless oil (26.24 g, 49%). $^1$H-NMR; δ (CDCl$_3$), 7.78 (2H, m), 7.67 (2H, m), 5.28–5.05 (4H, br m), 4.54–4.35 (2H, br m), 3.03 (1H, m), 1.86 (1H, m), 1.68 (1H, m), 1.50 (9H, s), 1.49 (1H, m), 0.82 (3H, d, J=6.6 Hz) and 0.78 (3H, d, J=6.5 Hz).

STEP B

3R-tert-Butoxycarbonyl-5-methyl-2-phthalimidomethyl-hexanoic acid

2-Benzyloxycarbonyl-3R-tert-butoxycarbonyl-5-methyl-2-phthalimidomethyl-hexanoic acid benzyl ester (26.24 g, 42.8 mmol) was deprotected by catalytic hydrogenolysis in ethanol, according to the method described in Example 32 (Step B). The solvent was removed under reduced pressure, the residue was dissolved in toluene (250 ml) and NMM (4.33 g, 42.8 mmol) was added. The mixture was heated under reflux for 2 h. Solvents were evaporated and the remaining oil was dissolved in ethyl acetate and the solution was washed with 5% citric acid (2×200 ml) and brine (200 ml), dried over anhydrous magnesium sulphate and filtered. The solvent was removed, leaving the desired product as a yellow foam (16.58 g, including residual solvent) which was used directly in Step C.

$^1$H-NMR; δ (CDCl$_3$), 7.83 (2H, m), 7.72 (10H, m), 4.12 (1H, m), 3.83 (1H, m), 3.21 (1H, m), 2.72 (1H, m), 1.81–1.55 (2H, br m), 1.48 (9H, s), 1.31 (1H, m) and 0.92 (6H, m).

STEP C

3R-tert-Butoxycarbonyl-5-methyl-2-phthalimidomethyl-hexanoic acid benzyl ester 3R-tert-Butoxycarbonyl-5-methyl-2-phthalimidomethyl-hexanoic acid (16.58 g, 42.56 mmol) was dissolved in dry DMF and placed under a blanket of argon. The solution was cooled in an ice bath, benzyl bromide (5.56 ml, 46.82 mmol) and anhydrous sodium carbonate (4.96 g, 46.82 mmol) were added and the mixture was left to stir overnight at room temperature. The solvent was removed under reduced pressure and the residual oil was dissolved in diethyl ether (300 ml) and washed successively with water (2×200 ml), 1M hydrochloric acid (2×200 ml) and brine (200 ml). The organic phase was dried (anhydrous magnesium sulphate), filtered and evaporated to a crude yellow oil which was purified by column chromatography (silica gel, gradient elution, 30Æ50% diethyl ether in hexane). The desired product was isolated as a pale yellow oil (18.2 g, 89%; 3:2 mixture of diastereoisomers). $^1$H-NMR; δ (CDCl$_3$), 7.78 (2H, m), 7.67 (2H, m), 7.24 (5H, m), 5.05 (2H, m), 4.18–4.04 (1H, br m), 3.81 (1H, br m), 3.15 (1H, m), 2.73 (1H, m), 1.72–1.53 (2H, br m), 1.50 (5.4H, s), 1.41 (3.6H, s), 1.11 (1H, m) and 0.90 (6H, m).

STEP D

3R-Carboxy-5-methyl-2-phthalimidomethyl-hexanoic acid benzyl ester 3R-tert-Butoxycarbonyl-5-methyl-2-phthalimidomethyl-hexanoic acid benzyl ester was deprotected by acidolysis with TFA according to the procedure described in Example 1 (Step G). The product was isolated as a pale yellow oil (16.54 g, including residual solvent) and was used in Step E without further purification. $^1$H-NMR; δ (CDCl$_3$, 3:2 mixture of diastereoisomers), 8.28 (1H, br s), 7.78 (2H, m), 7.68 (2H, m), 7.25 (5H, m), 5.08 (2H, m), 4.15 (1H, m), 3.89 (1H, m), 3.25 (1H, m), 2.88 (1H, m), 1.82–1.52 (2H, br m), 1.25 (1H, m), and 0.89 (6H, m).

STEP E

3R-(2,2-Dimethyl-1S-pyridin-2-ylcarbamoyl-propylcarbamoyl)-5-methyl-2RS-phthalimidomethylhexanoic acid benzyl ester 3R-Carboxy-5-methyl-2-phthalimidomethyl-hexanoic acid benzyl ester was dissolved in ethyl acetate (200 ml), HOBt (5.21 g, 38.58 mmol) and EDC (7.40 g, 38.58 mmol) were added and the reaction mixture was stirred for 3.5 h to ensure complete formation of the activated ester. L-tert-Leucine-N-(2-pyridyl)amide (7.32 g, 35.36 mmol) was added and the reaction mixture was heated at reflux overnight. The solution was cooled before washing successively with 5% aq. sodium bicarbonate, (2×200 ml) and water (2×200 ml). The organic phase was dried (anhydrous magnesium sulphate), filtered and evaporated under reduced pressure to leave a yellow foam. Column chromatography (silica gel, gradient elution, 20Æ50% ethyl acetate in hexane) gave the desired product as an inseparable mixture of diastereoisomers (16.89 g, 86%). $^1$H-NMR; δ (CDCl$_3$), 9.76 (0.6H, s), 9.58 (0.4H, s), 8.45 (1H, m), 8.25 (1H, m), 7.85–7.60 (5H, br m), 7.23 (4H, m), 7.08 (2H, m), 5.05 (2H, m), 4.76 (0.6H, m), 4.57 (0.4H, m), 4.03 (2H, m), 3.33 (0.6H, m), 3.22 (0.4H, m), 2.85 (0.6H, m), 2.70 (0.4H, m), 1.78 (1H, m), 1.55 (2H, m), 1.10 (5.5H, s), 1.05 (3.5H, s) and 0.93–0.67 (6H, br m).

STEP F

3R-(2,2-Dimethyl-1S-pyridin-2-ylcarbamoyl-propylcarbamoyl)-5-methyl-2RS-phthalimidomethylhexanoic acid 3R-(2,2-Dimethyl-1S-pyridin-2-ylcarbamoyl-propylcarbamoyl)-5-methyl-2RS-phthalimidomethylhexanoic acid benzyl ester (5.08 g, 8.3 mmol) was deprotected by catalytic transfer hydrogenolysis in ethanol, according to the method described in Example 1 (Step E). The product was isolated as a white solid (4.34 g 75%) following solvent evaporation and was used without further purification. $^1$H-NMR; δ (CD$_3$OD, 3:2 mixture of diastereoisomers), 8.31 (1H, m), 8.08 (1H, m), 7.81 (5H, m), 7.11 (1H, m), 4.61 (0.6H, s), 4.52 (0.4H, s), 4.11 (0.6H, m), 3.99 (0.4H, m), 3.76 (1H, m), 3.14–2.85 (2H, br m), 1.73 (1H, m), 1.53 (2H, m), 1.14 (5.5H, s), 1.08 (3.5H, s), 0.92 (3.6H, m) and 0.82 (2.4H, m).

STEP G

3R-(2,2-Dimethyl-1S-pyridin-2-ylcarbamoyl-propylcarbamoyl)-5-methyl-2RS-phthalimidomethylhexanohydroxamic acid 3R-(2,2-Dimethyl-1S-pyridin-2-ylcarbamoyl-propylcarbamoyl)-5-methyl-2RS-phthalimidomethylhexanoic acid was converted to the corresponding hydroxamic acid by the method described in Example 32 (Step D). The solvent was removed under reduced pressure and the residue was dissolved in ethyl acetate and washed in 5% aq. sodium hydrogen carbonate, 5% citric acid and brine, dried (anhydrous magnesium sulphate), filiitered and evaporated. The product was purified by column chromatography (acid-washed silica, gradient elution 0–5% methanol in dichloromethane). Yield: 2.10 g (63%). $^1$H-NMR; δ ((CD$_3$)$_2$SO, 2:1 mixture of diastereoisomers), 8.42–8.15 (2H, br m), 7.65 (5H, m), 6.99 (1H, m), 4.68 (0.75H, m), 4.55 (0.25H, m), 4.07 (1H, m), 3.52 (1H, m), 2.99–2.72 (2H, br m), 1.34–1.24 (3H, br m), 1.17 (6H, s), 0.95 (3H, s), 0.79 (3H, m) and 0.68 (3H, m).

EXAMPLE 38

3R-(2,2-Dimethyl-1S-(N-oxy-pyridin-2-yl) carbamoyl-propylcarbamoyl)-2S-hydroxy-5-methylhexanohydroxamic acid

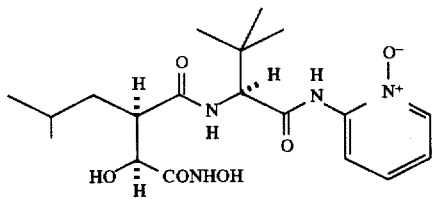

3R-(2,2-Dimethyl-1S-pyridin-2-ylcarbamoyl-propylcarbamoyl)-2S-hydroxy-5-methylhexanohydroxamic acid (Example 8) (100 mg, 0.25 mmol) was dissolved in dichloromethane (10 ml) and mCPBA (48 mg, 0.28 mmol) was added. The reaction mixture was stirred at room temperature for 3 h, after which TLC analysis revealed that all of the starting material had been converted to a more polar ferric chloride positive compound. The solvent was removed under reduced pressure and the residue was purified by column chromatography (acid-washed silica gel, 10% methanol in dichloromethane) to afford the title compound as a glassy solid (60 mg, 58%). m.p. 150–152∞C. $^1$H-NMR; δ ((CD$_3$)$_2$SO), 8.42–8.26 (2H, m), 8.19 (1H, d, J=7.9 Hz), 7.53–7.43 (1H, m), 7.16–7.06 (1H, m), 4.47 (1H, d, J=7.8 Hz), 4.02 (1H, d, J=6.1 Hz), 2.96–2.84 (1H, m), 1.63–1.38 (2H, m), 1.26–1.07 (1H, m), 0.99 (9H, s), 0.82 (3H, d, J=6.4 Hz) and 0.75 (3H, d, J=6.4 Hz). $^{13}$C-NMR; δ ((CD$_3$)$_2$SO), 173.7, 170.3, 168.7, 143.2, 137.4, 127.2, 119.5, 114.5, 71.2, 62.1, 47.5, 37.2, 33.6, 26.6, 25.2, 23.6 and 21.8. IR (KBr disc); $v_{max}$ 3258, 2958, 1652, 1510 and 1430 cm$^{-1}$.

BIOLOGICAL EXAMPLE

The following table compares the in vitro potencies of compounds of the present invention against those of similar compounds known in the art where R$_4$=Me (Comparators 1 to 5).

Comparator 1: 5-Methyl-3R-(1S-methylcarbamoyl-2-phenylethylcarbamoyl)-hexanohydroxamic acid.

Comparator 2: 3R-(2,2-Dimethyl-1S-methylcarbamoyl-propylcarbamoyl)-2S-hydroxy-5-methylhexanohydroxamic acid.

Comparator 3: 3R-(2,2-Dimethyl-1S-methylcarbamoyl-propylcarbamoyl)-5-methylhexanohydroxamic acid.

Comparator 4: 2S-Hydroxy-3R-(1S-methylcarbamoyl-2-phenylethylcarbamoyl)-5-methylhexanohydroxamic acid.

Comparator 5: 2S-Hydroxy-3R-(1S-methylcarbamoyl-3-methyl-butylcarbamoyl)-5-methylhexanohydroxamic acid.

The potency of compounds of the invention as inhibitors of collagenase was determined by the procedure of Cawston and Barrett, (Anal. Biochem, 99, 340–345, 1979), hereby incorporated by reference, whereby a 1 mM solution of the compound being tested, or a dilution thereof, was incubated at 37° for 16 hours with collagen and collagenase (buffered with 25 mM Hepes, pH 7.5 containing 5mM CaCl$_2$, 0.05% Brij 35 and 0.02% NaN$_3$). The collagen was acetylated $^{14}$C collagen prepared by the method of Cawston and Murphy, (Methods in Enzymology, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity (IC$_{50}$).

The potency of compounds of the invention as inhibitors of stromelysin was determined by the procedure of Cawston et al. (Biochem. J., 195, 159–165, 1981), hereby incorporated by reference, whereby a 1 mM solution of the compound being tested, or a dilution thereof, was incubated at 37° for 16 hours with stromelysin and $^{14}$C acetylate casein (buffered with 25 mM Hepes, pH 7.5 containing 5 mM CaCl$_2$, 0.05% Brij 35 and 0.02% NaN$_3$). The casein was acetylated $^{14}$C casein prepared by the method of Cawston et al (ibid). The stromelysin activity in the presence of 1 mM of the test compound, or a dilution thereof, was compared to activity in a control devoid of inhibitor and the result reported below as that of inhibitor concentration effecting 50% inhibition of the stromelysin activity (IC$_{50}$).

The potency of compounds of the invention as inhibitors of 72 kDa gelatinase was determined by a procedure based on the method of Sellers et. al, Biochem. J, 171, 493–496 (1979). 72 kDa gelatinase, derived from RPMI-7951 cells was purified by gelatin-agarose chromatography. The enzyme was activated by incubation with aminophenyl mercuric acetate and approximately 0.05 units was incubated with 50 μg [$^{14}$C]-radiolabellet gelatin in an appropriate buffer for 16 hours at 37° C. At the end of the incubation 50 μg bovine serum albumin, together with trichloroacetic acid (final concentration 16%) were added to stop the reaction and to precipitate any undegraded substrate. The reaction tubes were placed on ice for 15 minutes before centrifugation at 10,000 g for 15 minutes to sediment the precipitated substrate. A 200 μl aliquot of the reaction supernatant was removed and the radioactivity determined by liquid scintillation counting. The effect of the inhibitors was determined by reference to a dose response curve. The IC$_{50}$ (the concentration of inhibitor required to cause a 50% decrease in enzyme activity) was obtained by fitting a curve to the data and computing the concentration of inhibitor required to achieve 50% inhibition of the enzyme. For each IC$_{50}$ determination, the effect on gelatinase activity of at least 8 concentrations of the inhibitor were examined. The inhibitors were dissolved and diluted in DMSO.

| | In vitro inhibitory activity IC$_{50}$ nM | | |
|---|---|---|---|
| TEST COMPOUND | Collagenase | 72 kDa Gelatinase | Stromelysin |
| Example 1 | 20 | 60 | 10 |
| Comparator 1 | 15 | 10 | 350 |
| Example 4 | 2 | 5 | 9 |
| Example 8 | 6 | 15 | 30 |
| Example 17 | 2 | 30 | 20 |
| Comparator 2 | 5 | 6 | 200 |
| Example 2 | 30 | 30 | 15 |
| Example 3 | 40 | 30 | 150 |
| Comparator 3 | 10 | 8 | 700 |
| Example 6 | 30 | 8 | 3 |
| Comparator 4 | 15 | 3 | 200 |
| Example 5 | 30 | 6 | 5 |
| Comparator 5 | 8 | not done | 90 |

EXAMPLE 39

N¹-[2,2-Dimethyl-1S-(pyridin-2-ylcarbamoyl)-propyl]-N⁴-hydroxy-2 R-isobutyl-3S-methoxy-succinamide

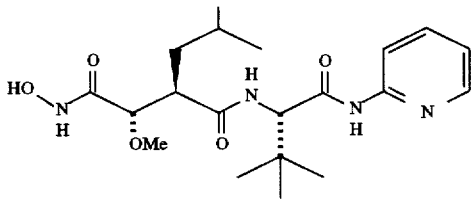

STEP A

2S-Hydroxy-3R-isobutyl-succinic acid dimethyl ester 2R-(2,2-Dimethyl-5-oxo-[1,3]dioxolan-4S-yl)-4-methyl-pentanoic acid (75.0 g, 0.326 mmol), prepared as described in WO 95/19961, was dissolved in methanol (500 ml) and cooled to 0° C. and the resulting solution was saturated with hydrogen chloride gas. The reaction mixture was allowed to warm to room temperature and stirred overnight. The solvent was removed under reduced pressure and the residue was dissolved in dichloromethane and washed successively with sat. sodium hydrogen carbonate and brine. The organic phase was dried over anhydrous magnesium sulphate, filtered and evaporated to dryness under reduced pressure to give the title compound as a yellow oil (53 g, 75%). ¹H-NMR; δ (CDCl₃), 4.10 (1H, d, J=4.0 Hz), 3.60 (3H, s), 3.50 (3H, s), 3.18 (br s), 2.78 (1H, m), 1.61–1.40 (2H, m), 2H, m), 1.28 (1H, m) and 0.76–0.73 (6H, m).

STEP B

2R-Isobutyl-3S-methoxy-succinic acid dimethyl ester

2S-Hydroxy-3R-isobutyl-succinic acid dimethyl ester (23.9 g, 110 mmol) was dissolved in DMF (200 ml) and distillediodomethane (8.2 ml, 132 mmol) was added, followed by silver (I) oxide (27.95 g, 121 mmol). The reaction was stirred for 7 days at room temperature with the exclusion of light. The solvent was removed under reduced pressure and the residue was purified by column chromatography (silica gel, dichloromethane as eluent) to give the title compound as a viscous yellow oil (19.16 g, 75%). ¹H-NMR; δ (CDCl₃), 3.83 (1H, d, J=7.5 Hz), 3.71 (3H, s), 3.62 (3H, s), 3.30 (3H, s), 2.85 (1H, m), 1.65–1.39 (2H, m), 1.10 (1H, m) and 0.83–0.81 (6H, m).

STEP C

2R-Isobutyl-3S-methoxy-succinic acid dilithium salt

Lithium hydroxide (1.76 g, 42.0 mmol) was added to a solution of 2R-isobutyl-3S-methoxy-succinic acid dimethyl ester (4.70 g, 20.0 mmol) in methanol (30 ml) and water (30 ml). The reaction mixture was stirred at room temperature for 2 hours then the solvents were removed under reduced pressure to give the title compound as a yellow solid (4.40 g, quant.). ¹H-NMR; δ (CD₃OD), 3.52 (1H, d, J=5.1 Hz), 3.27 (3H, s), 2.65 (1H, m), 1.56–1.53 (2H, m), 1.31 (1H, m) and 0.82–0.78 (6H, m).

STEP D

2R-Isobutyl-3S-methoxy-succinic acid 4-methyl ester

2R-Isobutyl-3S-methoxy-succinic acid dilithium salt (25.14 g, 116 mmol) was dissolved in dry THF (150 ml) and the solution was cooled to 0° C. Trifluoroacetic anhydride (30 ml) was added and the mixture was stirred at 0° C. for a further 4 hours. The solvent was removed under reduced pressure and the residue was dissolved in anhydrous methanol (200 ml) at 0° C. and the solution was stirred overnight at room temperature. The solvent was removed under reduced pressure to give the title compound as a yellow oil (54.3 g, including 2 equivalents of lithium trifluoroacetate), which was used without further purification in STEP E. ¹H-NMR; δ (CD₃OD), 7.71 (1H, d, J=7.5 Hz), 3.65 (3H, s), 3.24 (3H, s), 2.72 (1H, m), 1.56–1.42 (2H, m), 1.06 (1H, m) and 0.81–0.79 (6H, m).

STEP E

3R-[2,2-Dimethyl-1S-(pyridylcarbamoyl-propylcarbamoyl]-2S-methoxy-5-methyl-hexanoic acid methyl ester The product from STEP D (25.06 g, equivalent to 53.7 mmol 2R-isobutyl-3S-methoxy-succinic acid 4-methyl ester) was dissolved in DMF (200 ml) and the solution was cooled to 0° C. during the addition of HOBt (8.70 g, 53.7 mmol) followed by EDC (12.35 g, 64.4 mmol). The mixture stirred and allowed to warm to room temperature over 2 hours. The solution of active ester thus formed was cooled to 0° C., L-tert-leucine-N-(2-pyridyl)amide (11.11 g, 53.7 mmol), prepared as described in WO 95/19961 was added and the mixture was stirred overnight at room temperature. The solvent was removed under reduced pressure and the residue was dissolved in ethyl acetate. The solution was washed successively with 1M sodium carbonate solution, and brine, dried over anhydrous magnesium sulphate, filtered and evaporated to dryness. The residue was purified by column chromatography (silica gel, 0 to 5% methanol in dichloromethane) to afford the title compound as a white solid (13.41 g, 61%). ¹H-NMR; δ (CDCl₃), 9.61 (1H, s), 8.47 (1H, m), 8.24 (1H, d, J=8.4 Hz), 7.74 (1H, m), 7.07 (1H, m), 6.97 (1H, d, J=8.9 Hz), 4.64 (1H, d, J=8.9 Hz), 4.01 (1H, d, J=7.6 Hz), 3.76 (3H, s), 3.41 (3H, s), 2.75 (1H, m), 1.79 (1H, m), 1.51 (1H, m), 1.11 (1H, m), 1.02 (9H, s), 0.84 (3H, d, J=6.3 Hz), and 0.82 (3H, d, J=6.3 Hz).

STEP F

3R-[2,2-Dimethyl-1S-(pyridin-2-ylcarbamoyl)-propylcarbamoyl]-2S-methoxy-5-methyl-hexanoic acid lithium salt 3R-[2,2-Dimethyl-1S-(pyridin2-ylcarbamoyl)-propylcarbamoyl]-2S-methoxy-5-methyl-hexanoic acid methyl ester (13.4 g, 32.9 mmol) was dissolved in a mixture of THF (265 ml) and water (65 ml) and lithium hydroxide monohydrate (1.396 g, 33.3 mmol) was added. The solution was stirred at room temperature for 2 hours then evaporated under reduced pressure to provide a yellow oil which was dried further by azeotroping with toluene. The product (13.4 g, containing residual solvent) was used immediately without further purification. ¹H-NMR; δ (CD₃OD, 3.5:1 mixture of diastereoisomers), 8.31 (1H, m), 7.99 (1H, d, J=8.3 Hz), 7.66 (1H, m), 7.00 (1H, m), 4.49 (0.23H, s; minor diastereoisomer), 4.37 (0.77H, s, major diastereoisomer), 3.68 (0.23H, d, J=7.6 Hz; minor diastereoisomer), 3.52 (0.77H, d, J=7.6 Hz; major diastereoisomer), 3.21 (0.69H, s; minor diastereoisomer), 3.20 (2.31H, s, major diastereoisomer), 2.64 (1H, m), 1.53 (2H, br m), 1.18 (1H, m), 1.01 (9H, s), 0.85 (3H, d, J=6.4 Hz) and 0.81 (3H, d, J=6.3 Hz).

STEP G

N⁴-Benzyloxy-N¹-[2,2-dimethyl-1S-(pyridin-2-ylcarbamoyl)-propyl]-2R-isobutyl-3S-methoxy-succinamide The product from STEP F (13.4 g, ca. 33 mmol) was dissolved in dry DMF (250 ml) and placed under argon and cooled to −10° C. with stirring. Ethyl chloroformate (3.47 ml, 36 mmol) was added dropwise, followed by NMM (1.8 ml, 16.5 mmol). The mixture was stirred for 30 minutes before dropwise addition of O-benzylhydroxylamine (6 g, 49 mmol) in DMF (10 ml). The reaction mixture was allowed to warm to room temperature and stirred overnight. The solvent was removed under reduced pressure and the residue was partitioned between ethyl acetate and brine. The organic layer was washed with 1M sodium carbonate solution, dried over magnesium sulphate, filtered and evaporated. The residue was purified by flash chromatography (silica gel, 5% methanol in dichloromethane). Fractions containing the desired product were pooled and evaporated. The product was triturated with diethyl ether to remove slight coloured impurity. Yield: 9.44 g (58%, >10:1 mixture of diastereoisomers). $^1$H-NMR; δ (CDCl$_3$, major diastereoisomer), 10.26 (1H, s), 9.93 (1H, s), 8.32 (1H, m), 8.23 (1H, d, J=8.2 Hz), 7.63 (1H, m), 7.25 (5H, m), 7.12 (1H, d, J=9.2 Hz), 7.02 (1H, m), 4.94 (1H, d, J=10.8 Hz), 4.76 (2H, d, J=3.8 Hz), 3.88 (1H, d, J=5.5 Hz), 3.32 (3H, s), 2.91 (1H, m), 1.72 (1H, m), 1.55 (1H, m), 1.35 (1H, m), 1.02 (9H, s), 0.89 (3H, d, J=6.5 Hz) and 0.85 (3H, d, J=6.5 Hz).
STEP H $N^1$-[2,2-Dimethyl-1S-(pyridin-2-ylcarbamoyl)-propyl]-$N^4$-hydroxy-2R-isobutyl-3S-methoxy-succinamide $N^4$-Benzyloxy-$N^1$-[2,2-dimethyl-1S-(pyridin-2-ylcarbamoyl)-propyl]-2R-isobutyl-3S-methoxy-succinamide was dissolved in a mixture of methanol (75 ml) and ethanol (75 ml) and placed under an argon atmosphere. 10% palladium on charcoal was added and hydrogen gas was bubbled through the solution for 2 hours, at which time TLC analysis revealed that all of the starting material had been consumed. The system was purged with argon and the catalyst was removed by filtration. The solvents were removed under reduced pressure to provide the title compound as a white solid (8.8 g, quant.; 12:1 mixture of diastereoisomers). m.p. 163°–164 ° C. $^1$H-NMR; δ ((CD$_3$)$_2$SO), 10.67 (1H, s), 10.13 (1H, s), 8.90 (1H, s), 8.15 (1H, m), 7.89 (1H, d, J=8.4 Hz), 7.81 (1H, d, J=8.8 Hz), 7.60 (1H, m), 6.93 (1H, m), 4.53 (0.12H, d, J=9.4 Hz), 4.43 (0.88H, d, J=8.8 Hz), 3.74 (0.12H, d, J=10.0 Hz), 3.32 (0.88H, d, J=9.8 Hz), 2.98 (0.3H, s), 2.96 (2.64H, s), 2.78 (1H, m), 1.23 (2H, m), 0.84 (10H, s and m), 0.65 (3H, d, J=6.4 Hz) and 0.56 (3H, d, J=6.3 Hz). $^{13}$C-NMR; δ (CD$_3$OD), 172.6, 170.0, 166.0, 151.5, 147.9, 136.0, 119.5, 113.6, 61.2, 60.6, 56.7, 46.2, 37.0, 34.0, 26.5, 25.2, 23.7 and 21.7. IR; ν$_{max}$ (KBr), 3255, 2957, 1700, 1645, 1524, 1467, 1435, 1370, 1301, 1213 and 1152 cm$^{-1}$. Found: C 58.40, H 7.92, N 13.61%; $C_{20}H_{32}N_4O_5$·0.2H$_2$O requires C 58.29, H 7.92, N 13.60%.

We claim:

1. A compound of formula (I)

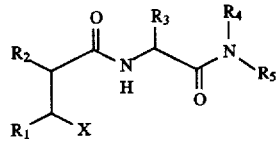

(I)

wherein

X is a —CO$_2$H or —CONHOH group;

R$_1$ is hydrogen; (C$_1$–C$_6$)alkyl; (C$_2$–C$_6$)alkenyl; phenyl; substituted phenyl; phenyl(C$_1$–C$_6$)alkyl; substituted phenyl(C$_1$–C$_6$)alkyl; heterocyclyl; substituted heterocyclyl; heterocyclyl(C$_1$–C$_6$)alkyl; substituted heterocyclyl(C$_1$–C$_6$)alkyl; a group BSO$_n$A— wherein n is 0, 1 or 2 and B is hydrogen or a (C$_1$–C$_6$)alkyl, phenyl, substituted phenyl, heterocyclyl, (C$_1$–C$_6$)acyl, phenacyl or substituted phenacyl group, and A represents (C$_1$–C$_6$)alkyl; amino; protected amino; acylamino; OH; SH; (C$_1$–C$_6$)alkoxy; (C$_1$–C$_6$)alkylamino; di-(C$_1$–C$_6$)alkylamino; (C$_1$–C$_6$)alkylthio; aryl(C$_1$–C$_6$)alkyl; amino(C$_1$–C$_6$)alkyl; hydroxy(C$_1$–C$_6$)alkyl, mercapto(C$_1$–C$_6$)alkyl or carboxy(C$_1$–C$_6$)alkyl wherein the amino-, hydroxy-, mercapto- or carboxyl-group are optionally protected or the carboxyl-group amidated; lower alkyl substituted by carbamoyl, mono (lower alkyl)carbamoyl, di(lower alkyl)carbamoyl, di(lower alkyl)amino, or carboxy-lower alkanoylamino;

R$_2$ is a (C$_1$–C$_6$)alkyl, (C$_2$–C$_6$)alkenyl, (C$_2$–C$_6$)alkynyl, phenyl(C$_1$–C$_6$)alkyl, heteroaryl(C$_1$–C$_6$)alkyl, cycloalkyl(C$_1$–C$_6$)alkyl or cycloalkenyl(C$_1$–C$_6$)alkyl group, any one of which may be optionally substituted by one or more substituents selected from (C$_1$–C$_6$) alkyl, —O(C$_1$–C$_6$)alkyl, —S(C$_1$–C$_6$)alkyl, halo and cyano (—CN);

R$_3$ is:

(C$_1$–C$_6$)alkyl, benzyl, hydroxybenzyl, benzyloxybenzyl, (C$_1$–C$_6$)alkoxybenzyl, or benzyloxy(C$_1$–C$_6$)alkyl group; or the characterising group of a natural α amino acid, in which any functional group may be protected, any amino group may be acylated and any carboxyl group present may be amidated; or a group -(Alk)$_n$R$_6$ where Alk is a (C$_1$–C$_6$)alkyl or (C$_2$–C$_6$)alkenyl group optionally interrupted by one or more —O—, or —S— atoms or —N(R$_7$)— groups where R$_7$ is a hydrogen atom or a (C$_1$–C$_6$) alkyl group, n is 0 or 1, and R$_6$ is an optionally substituted cycloalkyl or cycloalkenyl group; or a benzyl group substituted in the phenyl ring by a group of formula —OCH$_2$COR$_8$ where R$_8$ is hydroxyl, amino, (C$_1$–C$_6$)alkoxy, phenyl(C$_1$–C$_6$)alkoxy, (C$_1$–C$_6$)alkylamino, di((C$_1$–C$_6$)alkyl)amino, phenyl (C$_1$–C$_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid;

a heterocyclic(C$_1$–C$_6$)alkyl group, either being unsubstituted or mono- or di-substituted in the heterocyclic ring with halo, nitro, carboxy, (C$_1$–C$_6$)alkoxy, cyano, (C$_1$–C$_6$)alkanoyl, trifluoromethyl(C$_1$–C$_6$)alkyl, hydroxy, formyl, amino, (C$_1$–C$_6$)alkylamino, di-(C$_1$–C$_6$)alkylamino, mercapto, (C$_1$–C$_6$)alkylthio, hydroxy(C$_1$–C$_6$)alkyl, mercapto(C$_1$–C$_6$)alkyl or (C$_1$–C$_6$)alkylphenylmethyl; or a group CR$_a$R$_b$R$_c$ in which:

each of R$_a$, R$_b$ and R$_c$ is independently hydrogen, (C$_1$–C$_6$)alkyl, C$_2$–C$_6$)alkenyl, (C$_2$–C$_6$)alkynyl, phenyl(C$_1$–C$_6$)alkyl, ((C$_3$–C$_8$)cycloalkyl, the foregoing being subject to the proviso that R$_a$, R$_b$ and R$_c$ are not all hydrogen; or R$_c$ is hydrogen, (C$_1$–C$_6$)alkyl, (C$_2$–C$_6$)alkenyl, (C$_2$–C$_6$) alkynyl, phenyl(C$_1$–C$_6$)alkyl, or (C$_3$–C$_8$)cycloalkyl, and R$_a$ and R$_b$ together with the carbon atom to which they are attached from a 3- to 8-membered cycloalkyl or a 5- to 6-membered heterocyclic ring; or R$_a$, R$_b$ and R$_c$ together with the carbon atom to which they are attached form a tricyclic ring; or $R_a$ and $R_b$ are each independently $(C_1-C_6)$alkyl, $(C_2-C_6)$alkenyl, $(C_2-C_6)$alkynyl, phenyl$(C_1-C_6)$alkyl, or a group as defined for $R_c$ below other than hydrogen, or $R_a$ and $R_b$ together with the carbon atom to which they are attached form a 3- to 8-membered cycloalkyl or a 3- to 8-membered heterocyclic ring, and $R_c$ is hydrogen, —OH, —SH, halogen, —CN, —CO$_2$H, $(C_1-C_4)$perfluoroalkyl, —CH$_2$OH, —CO$_2(C_1-C_6)$alkyl, —O$(C_1-C_6)$alkyl, —O$(C_1-C_6)$alkenyl, —S$(C_1-C_6)$alkyl, —SO$(C_1-C_6)$alkyl, —SO$_2(C_1-C_6)$alkyl, —S$(C_2-C_6)$alkenyl, —SO$(C_2-C_6)$alkenyl, —SO$_2(C_2-C_6)$alkenyl or a group —Q—W wherein Q represents a bond or —O—, —S—, —SO— or —SO$_2$— and W represents a phenyl, phenylalkyl, ($(C_3-C_8)$cycloalkyl, $(C_3-C_8)$cycloalkylalkyl, $(C_4-C_8)$cycloalkenyl, $(C_4-C_8)$cycloalkenylalkyl, heteroaryl or heteroarylalkyl group, which group W may optionally be substituted by one or more substituents independently selected from, hydroxyl, halogen, —CN, —CO$_2$H, —CO$_2(C_1-C_6)$alkyl, —CONH$_2$, —CONH$(C_1-C_6)$alkyl, —CONH$(C_1-C_6$alkyl)$_2$, —CHO, —CH$_2$OH, $(C_1-C_4)$perfluoroalkyl, —O$(C_1-C_6)$alkyl, —S$(C_1-C_6)$alkyl, —SO$(C_1-C_6)$alkyl, —SO$_2(C_1-C_6)$alkyl, —NO$_2$, —NH$_2$, —NH$(C_1-C_6)$alkyl, NH$((C_1-C_6$(alkyl)$_2$, —NHCO$(C_1-C_6)$alkyl, $(C_1-C_6)$alkyl, $(C_2-C_6)$alkenyl, $(C_2-C_6)$alkynyl, ($(C_3-C_8)$cycloalkyl, $(C_4-C_8)$cycloalkenyl, phenyl or benzyl;

$R_4$ is a phenyl or 5- or 6-membered heteroaryl ring wherein any ring nitrogen atom may be oxidised as an N-oxide, which may be optionally fused to a benzene ring or to a 5-, 6- or 7-membered heterocyclic ring, and wherein any of the rings may be optionally substituted by:

(a) one or more substituents independently selected from hydroxyl, halogen, —CN, —CO$_2$H, —CO$_2$ $(C_1-C_6)$alkyl, —$(C_1-C_6)$alkyl—CO$_2(C_1-C_6)$alkyl, —CONH$_2$, —CONH$(C_1-C_6)$alkyl, —CON$((C_1-C_6)$alkyl)$_2$, —CHO, —CH$_2$OH, —$(C_1-C_4)$perfluoroalkyl, —O$(C_1-C_6)$alkyl, —S$(C_1-C_6)$alkyl, —SO$(C_1-C_6)$alkyl, —SO$_2(C_1-C_6)$alkyl, —NO$_2$, NH$_2$, —NH$(C_1-C_6)$alkyl, —N$((C_1-C_6)$alkyl)$_2$, and —NHCO$(C_1-C_6)$alkyl, or (b) a group selected from $(C_1-C_6)$alkyl, $(C_2-C_6)$alkenyl, $(C_2-C_6)$alkynyl, $(C_3-C_8)$cycloalkyl, $(C_4-C_8)$cycloalkenyl, phenyl, benzyl, heteroaryl or heteroarylmethyl any of which groups may be optionally substituted with one or more substituents selected from halogen, hydroxyl, amino, carboxyl, $(C_1-C_4)$perfluoroalkyl, $(C_1-C_6)$alkyl, —O$(C_1-C_6)$alkyl or —S$(C_1-C_6)$alkyl;

$R_5$ is hydrogen or a $(C_1-C_6)$alkyl group;
or a salt, hydrate or solvate thereof, PROVIDED THAT $R_4$ is not 2-pyridyl or 2-thiazolyl when $R_1$ is hydrogen, $R_2$ is n-pentyl, $R_3$ is iso-propyl, and $R_5$ is hydrogen.

2. A compound as claimed in claim 1 wherein the stereochemistry is as follows:

C atom carrying the $R_1$ and X groups is S,

C atom carrying the $R_2$ group is R,

C atom carrying the $R_3$ group is S.

3. A compound as claimed in claim 1 or claim 2 wherein $R_1$ is hydrogen, methyl, ethyl, hydroxyl, allyl, thienylsulphanylmethyl, thienylsulphinylmethyl, thienysulphonylmethyl and phthalimidomethyl.

4. A compound as claimed in claim 1 or 2 wherein $R_2$ is iso-butyl, n-pentyl, n-hexyl, n-heptyl, n-octyl, n-nonyl, n-decyl, cyclohexylpropyl, phenylpropyl, 4-chlorophenylpropyl, 4-methylphenylpropyl, 4-methoxyphenylpropyl, phenylbutyl, propyloxymethyl or propylsulphanyl.

5. A compound as claimed in claim 1 or 2 wherein $R_3$ is benzyl, iso-butyl, t-butyl, 1-benzylthio-1-methylethyl, or 1-mercapto-1-methylethyl.

6. A compound as claimed in claim 1 or 2 wherein $R_4$ is phenyl, napthyl, furanyl, thienyl, pyrrolinyl, tetrahydrofuranyl, imidazolyl, oxadiazolyl, thiazolyl, thiadiazolyl, pyridinyl, pyridinyl N-oxides, piperazinyl, indolyl, benzimidazolyl, benzotriazolyl, pyrazinyl, pyridazinyl, pyrimidinyl, dithianyl, benzo[b]thienyl, isoxazolyl or quinolinyl, any of which being optionally substituted by the substituents specified in relation to $R_4$ in claim 1.

7. A compound as claimed in claim 6 wherein $R_4$ is phenyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditribluoromethylphenyl, 2-aminophenyl, 3-aminophenyl, 4-aninophenyl, 2-N,N-dimethylaminophenyl, 3-N,N-dimethylaminophenyl, 4-N,N-dimethylamninophenyl, 2-hydroxyphenyl, 3-hydroxyphenyl, 4-hydroxyphenyl, 2-napthyl, furan-2-yl, thien-2-yl, pyrrol-2-yl, tetrahydrofuran-2-yl, imidazol-2-yl, thiazol-2-yl, 4-ethoxycarbonymethylthiazol-2-yl, 4-phenylthiazol-2-yl, 4,5-dimethylthiazol-2-yl, 5bromothiazol-2-yl, 4-tert-butylthiazol-2-yl, benzothiazol-2-yl, 1,2,4-oxadiazol-5-yl, 1,2,4-oxadiazol-3-yl, 3-methyl-1,2,4-oxadiazol-5-yl, 3-phenyl-1,2,4-oxadiazol-5-yl, 1,3,4-oxadiazol-2-yl, 1,2,4-thiadiazol-5-yl, 3-phenyl-1,2,4-thiadiazol-5-yl, 1,3,4-thiadiazol-2-yl, 5-methyl-1,3,4-thiadiazol-2-yl, pyridin-2-yl, pyridin-3-yl, pyridin-4-yl, N-oxides of pyridin-2-yl pyridin-3-yl and pyridin-4-yl, piperazin-1-yl, indol-2-yl, benzimidazol-2-yl, benzotriazol-2-yl, pyrazin-2-yl, 1,2-pyridazine-3-yl, 1,3-pyrimidin-5-yl, 1,3-dithian-2-yl, benzo[b]thien-2-yl, isoxazol-5-yl, quinolin-3-yl.

8. A compound as claimed in claim 1 or 2 in which $R_4$ is 3-methoxyphenyl, pyridin-2-yl, pyridin-3-yl, thiazol-2-yl, 4-ethoxycarbonylmethyl-thiazol-2-yl, 5-methyl-1,3,4-thiadiazol-2-yl and 4-tert-butylthiazol-2-yl.

9. A compound as claimed in claim 1 or 2 in which $R_5$ is hydrogen.

10. A compound selected from the group consisting of:

3R-(2,2-Dimethyl-1S-pyridin-2-ylcarbamoyl-propylcarbamoyl)-5-methyl-2S-propen-2-yl-hexanohydroxamic acid, 3R-(2,2-Dimethyl-1S-pyridin-2-ylcarbamoyl-propylcarbamoyl)-2S-hydroxy-5-methylhexanohydroxamic acid, 3R-(2,2-Dimethyl-1S-(5-methylthiadiazol-2-ylcarbamoyl)-propylcarbamoyl)-2S-hydroxy-5-methylhexanohydroxamic acid, 3R-(2,2-Dimethyl-1S-(3-methoxyphenyl)carbamoyl-propylcarbamoyl)-2S-hydroxy-5-methylhexanohydroxamic acid, 3R-(2,2-Dimethyl-1S-pyrid-3-ylcarbamoyl-propylcarbamoyl)-2S-hydroxy-5-methylhexanohydroxamic acid;

3R-(2,2-Dimethyl-1S-pyridin-2-ylcarbamoyl-propylcarbamoyl)-5-methyl-2S-phthalimidomethylhexanohydroxamic acid, 3R-(2,2-Dimethyl-1S-(thiazol-2-ylcarbamoyl)-propylcarbamoyl)-5-methyl-2S-propen-2-yl-hexanohydroxamic acid, 3R-(2,2-Dimethyl-1S-(thiazol-2-ylcarbamoyl)-propylcarbamoyl)-2S-hydroxy-5-methylhexanohydroxamic acid, and 3R-(2,2-Dimethyl-1S-(4-ethoxycarbonylmethylthiazol-2-ylcarbamoyl)-propylcarbamoyl)-2S-hydroxy-5-methylhexanohydroxamic acid, or a salt, solvate or hydrate thereof.

11. A compound selected from the group consisting of;

5-Methyl-3R-(2-phenyl-1S-phenylcarbamoyl-ethylcarbamoyl)-hexanohydroxamic acid, 3R-(2,2-Dimethyl-1S-phenylcarbamoyl-propylcarbamoyl)-5-methyl-hexanohydroxamic acid, 3R-(2,2-Dimethyl-1S-pyridin-2-ylcarbamoyl-propylcarbamoyl)-5-methyl-hexanohydroxamic acid, 3R-(2,2-Dimethyl-1S-phenylcarbamoyl-propylcarbamoyl)-2S-hydroxy-5-methylhexanohydroxamic acid, 2S-Hydroxy-3R-(3-methyl-1S-napth-2-ylcarbamoyl-butylcarbamoyl)-5-methyl-hexanohydroxamic acid, 2S-Hydroxy-3R-(3-methyl-1S-(4-methoxyphenyl)carbamoyl-butylcarbamoyl)-5-methyl-hexanohydroxamic acid, 3R-(2,2-Dimethyl-1S-(4-tertbutyl-2,6-dimethylphenyl)carbamoyl-propylcarbamoyl)-2S-hydroxy-5-methylhexanohydroxamic acid, 3R-(2,2-Dimethyl-1S-(4-methoxyphenyl)carbamoyl-propylcarbamoyl)-2S-hydroxy-5-methylhexanohydroxamic acid, 3R-(2,2-Dimethyl-1S-pyrid-4-ylcarbamoyl-propylcarbamoyl)-2S-hydroxy-5-methylhexanohydroxamic acid, 3R-(2,2-Dimethyl-1S-(4-hydroxyphenyl)carbamoyl-propylcarbamoyl)-2S-hydroxy-5-methylhexanohydroxamic acid, 3R-(2-Benzylthio-2-methyl-1S-(pyridin-2-ylcarbamoyl)propylcarbamoyl)-2S-hydroxy-5-methylhexanohydroxamic acid, 3R-(2,2-Dimethyl-1S-phenylcarbamoyl-propylcarbamoyl)-2S-hydroxy-5-phenylhexanohydroxamic acid, 3R-(2,2-Dimethyl-1S-(4,5-dimethylthiazol-2-ylcarbamoyl)-propylcarbamoyl)-2S-hydroxy-5-methylhexanohydroxamic acid, 3R-(2,2-Dimethyl-1S-(5-bromo-thiazol-2-ylcarbamoyl)-propylcarbamoyl)-2S-hydroxy-5-methylhexanohydroxamic acid, 3R-(2,2-Dimethyl-1S-(4-phenyl-thiazol-2-ylcarbamoyl)-propylcarbamoyl)-2S-hydroxy-5-methylhexanohydroxamic acid, 3R-(2,2-Dimethyl-1S-(4-tert-butylthiadiazol-2-ylcarbamoyl)-propylcarbamoyl)-2S-hydroxy-5-methylhexanohydroxamic acid, 3R-(2,2-Dimethyl-1S-phenylcarbamoyl-propylcarbamoyl)-5-methyl-2S-propen-2-yl-hexanohydroxamic acid, 3R-(2, 2-Dimethyl-1S-(4-methoxyphenylcarbamoyl)-propylcarbamoyl)-5-methyl-2S-propen-2-yl-hexanohydroxamic acid, 3R-(2-Benzylthio-2-methyl-1S-(pyridin-2-ylcarbamoyl)propylcarbamoyl)-5-methyl-2S-propen-2-yl-hexanohydroxamic acid, 3R-(2,2-Dimethyl-1S-(pyridin-3-ylcarbamoyl)-propylcarbamoyl)-5-methyl-2S-propen-2-yl-hexanohydroxamic acid, 3R-(2,2-Dimethyl-1S-(4-hydroxyphenylcarbamoyl)-propylcarbamoyl)-5-methyl-2S-propen-2-yl-hexanohydroxamic acid, 3R-(2,2-Dimethyl-1S-(3-methoxyphenylcarbamoyl)-propylcarbamoyl)-5-methyl-2S-propen-2-yl-hexanohydroxamic acid, 3R-(2,2-Dimethyl-1S-(pyridin-4-ylcarbamoyl)-propylcarbamoyl)-5-methyl-2S-propen-2-yl-hexanohydroxamic acid, 3R-(2,2-Dimethyl-1S-(2-methoxyphenylcarbamoyl)-propylcarbamoyl)-5-methyl-2S-thien-2-ylsulfanylmethyl-hexanohydroxamic acid, 3R-(2, 2-Dimethyl-1S-(pyridin-2--ylcarbamoyl)-propylcarbamoyl)-5-methyl-2S-thien-2-ylsulfanylmethyl-hexanohydroxamic acid, 3R-(2,2-Dimethyl-1S-(2,methoxyphenylcarbamoyl)-propylcarbamoyl)-5-methyl-2S-thien-2-ylsulfinylmethyl-hexanohydroxamic acid, 3R-(2,2-Dimethyl-1S-(pyridin-2-ylcarbamoyl)-propylcarbamoyl)-5-methyl-2S-thien-2-ylsulfinylmethyl-hexanohydroxamic acid, 3R-(2,2-Dimethyl-1S-phenylcarbamoyl-propylcarbamoyl)-2S-hydroxy-5-phenylhexanoic acid, and 3R-(2,2-Dimethyl-1S-(N-oxy-pyridin-2-yl)carbamoyl-propylcarbamoyl)-2S-hydroxy-5-methylhexanohydroxamic acid, or a salt, solvate or hydrate thereof.

12. A process for the preparation of a compound as claimed in claim 1 in which X is a hydroxamic acid group (—CONHOH), which process comprises:

(a) causing an acid of formula (II)

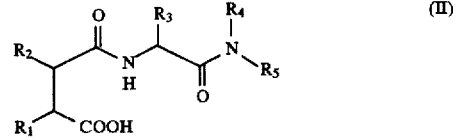

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in formula (I) except that any substituents in $R_1$, $R_2$, $R_3$, $R_4$ and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$ and $R_5$; or (b) deprotecting a diprotected hydroxamic acid derivative of formula (IIb)

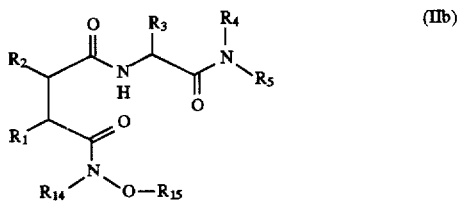

in which $R_1$, $R_2$, $R_3$, $R_4$ and $R_5$ are as defined in formula (I), $R_{14}$ is an amino protecting group and $R_{15}$ is a hydroxyl protecting group.

13. A process as claimed in claim 12 wherein in step (a) when $R_1$ in compound (I) is hydroxy the hydroxy group $R_1$ and the adjacent carboxyl group are simultaneously protected as a dioxalone of formula (IIa):

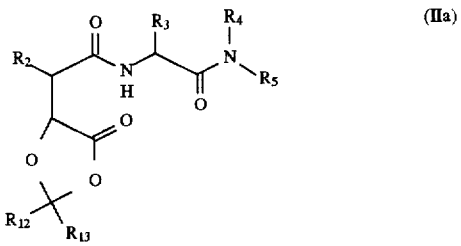

(IIa)

wherein the groups $R_{12}$ and $R_{13}$ are derived from a dioxalone forming reagent, and the dioxalone ring being is opened by the reaction with hydroxylamine to give the required hydroxamic acid derivative of formula (I).

14. A process for the preparation of a compound as claimed in claim 1 in which X is a carboxylic acid group (—COOH) which process comprises coupling an acid of formula (III) or an activated derivative thereof with an amine of formula (IV)

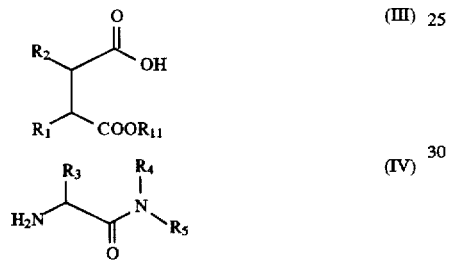

(III)

(IV)

wherein $R_1$, $R_2$, $R_3$, $R_4$ and $R_5$ are as defined in formula (I) except that any substituents in $R_1$, $R_2$, $R_3$, $R_4$ and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$, $R_2$, $R_3$, $R_4$ and $R_5$.

15. A process as claimed in claim 14 wherein when $R_1$ in compound (I) is hydroxy compound (II) has the formula (V):

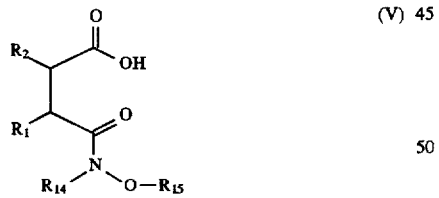

(V)

wherein $R_2$, $R_3$, $R_4$ and $R_5$ are as defined in formula (I) and the groups $R_{12}$ and $R_{13}$ are derived from a dioxalone forming reagent.

16. A method of treatment of diseases or conditions mediated by MMPs and/or TNF in mammals, which method comprises administering to the mammal an effective amount of a compound as claimed in claim 1 or 2.

17. A method as claimed in claim 16, wherein the diseases or conditions referred to is one mediated by an MMP.

18. A method as claimed in claim 16, wherein the diseases or conditions referred to are selected from the group consisting of rheumatoid arthritis, osteoarthritis, periodontitis, gingivitis, corneal ulceration, solid tumor growth and tumor invasion by secondary metastases, neovascular glaucoma, multiple sclerosis, and psoriasis.

19. A method as claimed in claim 16, wherein the diseases or conditions referred to is one mediated by TNF.

20. A method as claimed in claim 16, wherein the diseases or conditions referred to are selected from the group consisting of inflammation, fever, cardiovascular effects, haemorrhage, coagulation and acute phase response, cachexia and anorexia, an acute infection, a shock state, a graft versus host reaction and autoimmune disease.

21. A pharmaceutical or veterinary composition comprising a compound as claimed in claim 1 or 2 together with a pharmaceutically or veterinarily acceptable excipient or carrier.

22. A pharmaceutical or veterinary composition as claimed in claim 21 which is adapted for oral administration.

23. $N^1$-[2,2-dimethyl-1S-(pyridin-2-ylcarbamoyl)-propyl]-$N^4$-hydroxy-2R-isobutyl-3S-methoxy-succinamide, of the formula:

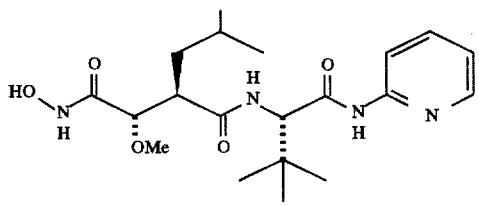

or a pharmaceutically acceptable salt, hydrate or solvate thereof.

24. A pharmaceutical composition comprising the compound of claim 23 or a pharmaceutically acceptable salt, hydrate or solvate thereof, together with a pharmaceutically acceptable carrier.

25. A composition as claimed in claim 24 which is adapted for oral administration.

26. A method for the treatment of multiple sclerosis in mammals, comprising administering to the mammal an amount of the compound of claim 23 or a pharmaceutically acceptable sale, hydrate or solvate thereof, effective to reduce the symptomatic and/or pathological manifestations of MS.

27. A method treatment of diseases or conditions mediated by MMPs and/or TNF in mammals, which method comprises administering to the mammal an effective amount of a compound of formula (I) shown in claim 1 wherein $R_4$ is 2-pyridyl, $R_1$ is hydrogen, $R_2$ is n-pentyl, $R_3$ is iso-propyl, and $R_5$ is hydrogen.

* * * * *